(12) United States Patent
Beyleveld et al.

(10) Patent No.: US 12,171,725 B2
(45) Date of Patent: Dec. 24, 2024

(54) ADHERENCE MONITORING METHOD AND DEVICE

(71) Applicant: ADHERIUM (NZ) LIMITED, Auckland (NZ)

(72) Inventors: Hein Beyleveld, Auckland (NZ); Michael James Gormack, Auckland (NZ); Tony Paul Kirker, Auckland (NZ); Benjamin Laurence Wilson, Auckland (NZ)

(73) Assignee: ADHERIUM (NZ) LIMITED, Auckland (NZ)

( * ) Notice: Subject to any disclaimer, the term of this patent is extended or adjusted under 35 U.S.C. 154(b) by 1287 days.

(21) Appl. No.: 16/634,356

(22) PCT Filed: Jul. 25, 2018

(86) PCT No.: PCT/NZ2018/050103
§ 371 (c)(1),
(2) Date: Jan. 27, 2020

(87) PCT Pub. No.: WO2019/022620
PCT Pub. Date: Jan. 31, 2019

(65) Prior Publication Data
US 2021/0085564 A1 Mar. 25, 2021

(30) Foreign Application Priority Data
Jul. 25, 2017 (NZ) ........................................ 734053

(51) Int. Cl.
*A61J 7/04* (2006.01)
*A61B 5/00* (2006.01)
*G16H 20/13* (2018.01)

(52) U.S. Cl.
CPC ............ *A61J 7/0418* (2015.05); *A61B 5/0022* (2013.01); *A61B 5/742* (2013.01); *G16H 20/13* (2018.01)

(58) Field of Classification Search
CPC ...... A61J 7/0418; A61B 5/0022; A61B 5/742; G16H 20/13
See application file for complete search history.

(56) References Cited

U.S. PATENT DOCUMENTS

| | | | | |
|---|---|---|---|---|
| 5,462,525 A | * | 10/1995 | Srisathapat | A61M 5/14276 604/67 |
| 6,651,651 B1 | * | 11/2003 | Bonney | A61M 15/008 128/200.23 |

(Continued)

FOREIGN PATENT DOCUMENTS

WO WO2007137991 A1 12/2007

OTHER PUBLICATIONS

International Search Report for PCT Patent App. No. PCT/NZ2018/050103 (Jul. 25, 2018).

(Continued)

*Primary Examiner* — Michael Collins
(74) *Attorney, Agent, or Firm* — KENEALY VAIDYA LLP

(57) ABSTRACT

In one aspect the invention provides an adherence monitoring device for a medication delivery device, the monitoring device including at least one inductive coil sensor which includes at least one inductive controller, at least two inductive coils including a first inductive coil coupled to the housing and a second inductive coil coupled to the housing. The first inductive coil is configured to exhibit a response to an inductive change and provide a first change signal in response to an inductive change, and the second inductive coil is configured to exhibit a response to the inductive change and provide a second change signal in response to (Continued)

the inductive change. The monitoring device also includes a processor configured to receive sensor data from the inductive controller representative of the first and second change signals provided by the first inductive coil and second inductive coil and to compare at least one characteristic of the first change signal and the second change signal to detect the occurrence of a medication usage event or a false triggering event.

20 Claims, 24 Drawing Sheets

(56) References Cited

U.S. PATENT DOCUMENTS

| | | | |
|---|---|---|---|
| 7,347,200 B2 * | 3/2008 | Jones | A61M 15/008 |
| | | | 128/200.23 |
| 9,607,261 B1 * | 3/2017 | Zonana | G06M 1/274 |
| 10,998,093 B2 * | 5/2021 | Sutherland | A61M 15/0091 |
| 11,724,070 B2 * | 8/2023 | Kinio | A61B 5/6852 |
| | | | 606/167 |
| 2021/0343404 A1 * | 11/2021 | Hunt | G16H 20/13 |

OTHER PUBLICATIONS

Written Opinion for PCT Patent App. No. PCT/NZ2018/050103 (Jul. 25, 2018).

* cited by examiner

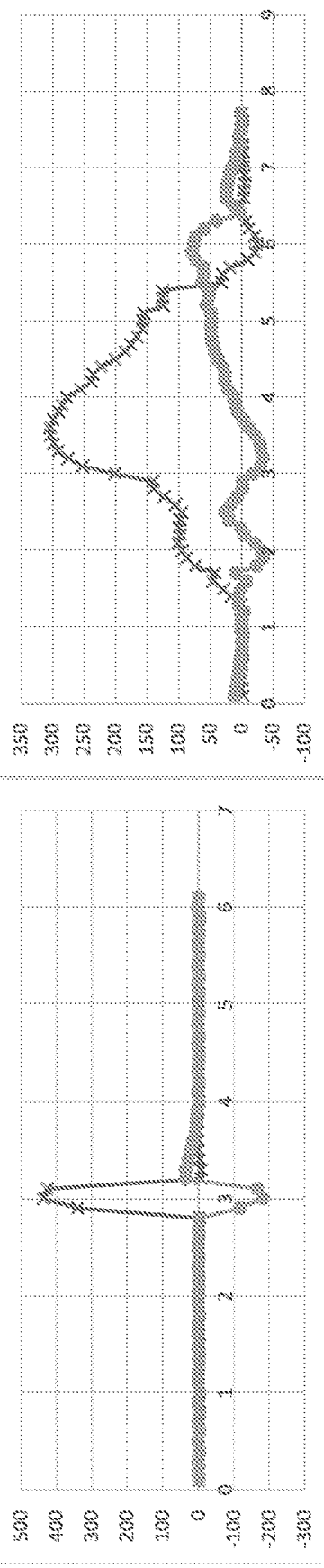
FIG. 18A
FIG. 18B
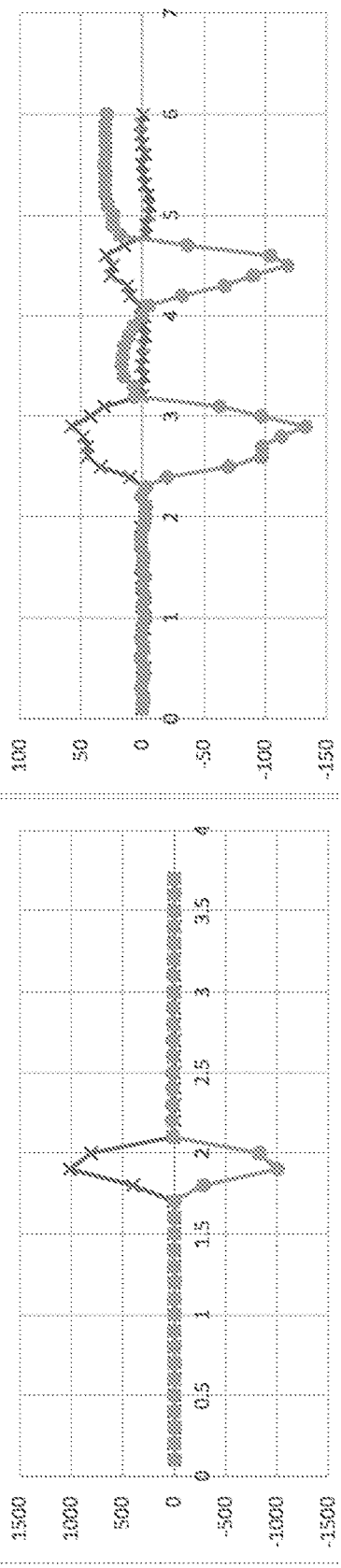
FIG. 18C
FIG. 18D

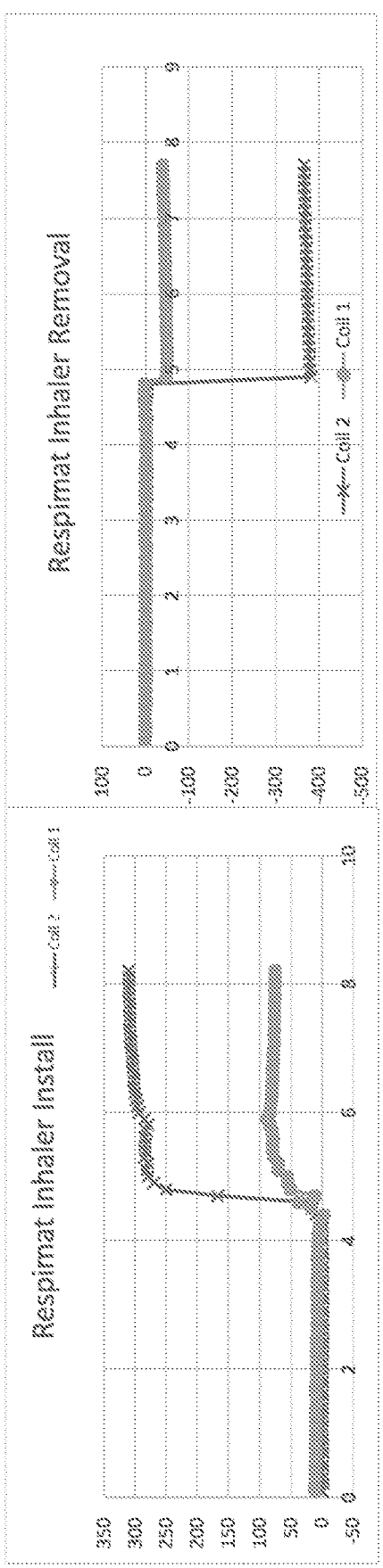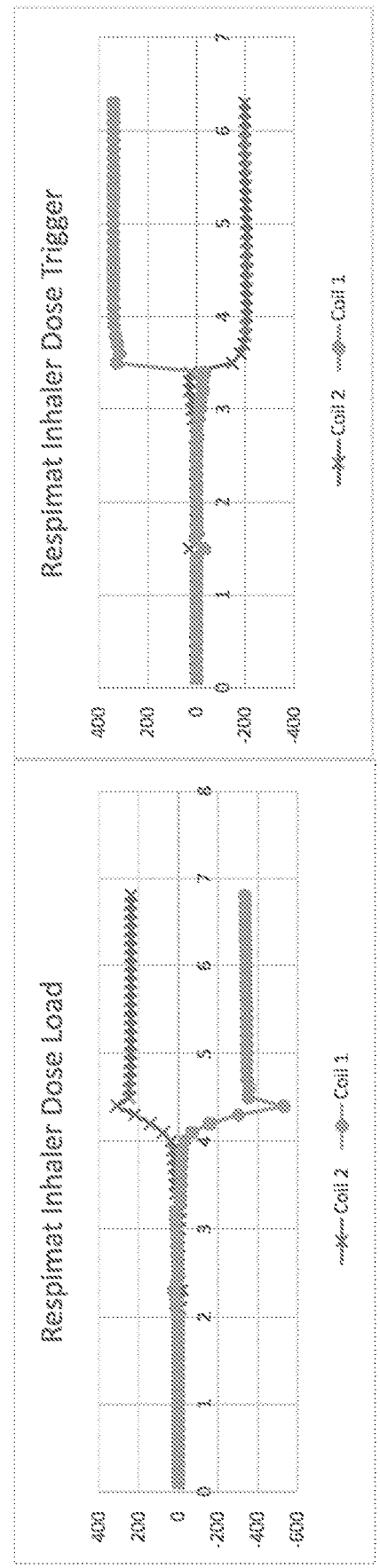
FIG. 19A
FIG. 19B
FIG. 19C
FIG. 19D

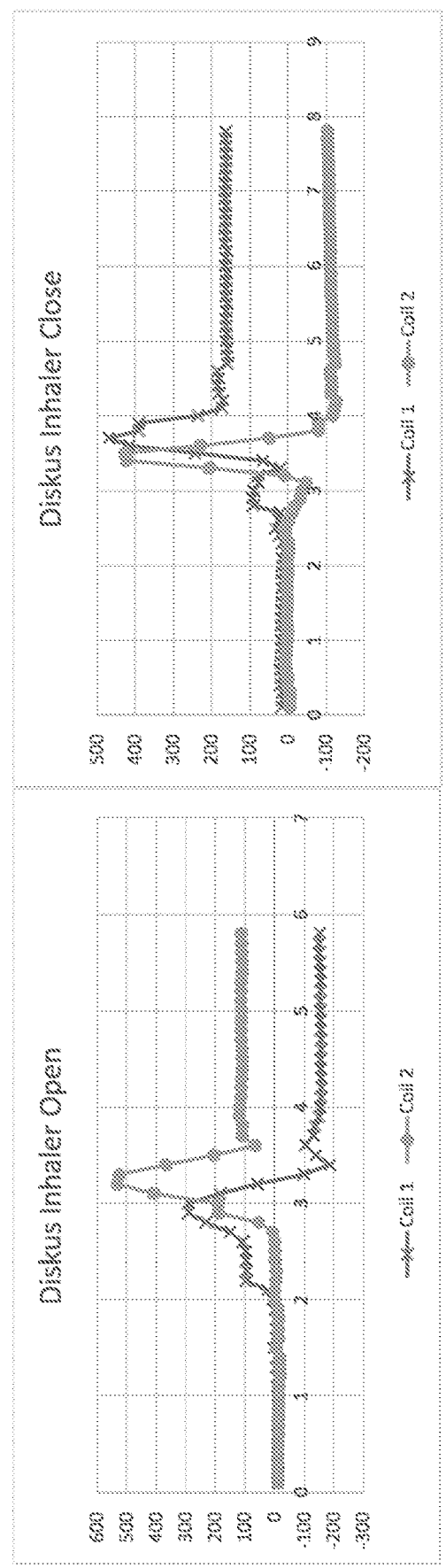

ADHERENCE MONITORING METHOD AND DEVICE

TECHNICAL FIELD

The present invention relates to methods, devices and systems for monitoring adherence to medication regimes.

BACKGROUND OF THE INVENTION

Non-adherence to medication regimes is a major healthcare problem. Many studies have shown that users frequently do not take their medication at the predetermined or prescribed times or in the required amounts. The consequences of this non-adherence can include reduced disease control, lower quality of life, lost productivity, hospitalisation and avoidable deaths. This represents a considerable cost to the users, as well as to the health care systems worldwide.

The problem affects patients across all areas of treatment where patients are responsible for chronic disease management by adhering to medication regimes prescribed to them by their healthcare professionals. Non- or low adherence affects, in particular, patients suffering from chronic cardiovascular, endocrine and respiratory conditions. Non-adherence affects users of inhaled, injected or oral medication.

To address this problem, there are now available a number of adherence monitoring devices, for example, for use with medication inhalers. The adherence monitoring devices include dose detection means and means for transmitting the adherence data gathered, either wirelessly or otherwise, to a device such as, for example, a docking station, smartphone, tablet or personal computer (belonging to the user or a healthcare professional) and further storage of the adherence data on a website database or cloud computing network. This adherence data may be transmitted in real time or at predetermined set times. Examples of patents which describe such technology are: U.S. Pat. No. 6,958,691 (Anderson et al.), U.S. Pat. No. 8,424,517 (Sutherland et al.) and U.S. Pat. No. 8,342,172 (Levy et al.), U.S. Pat. No. 5,363,842 (Mishelevich et al.), U.S. Pat. No. 8,464,707 (Jongejan et al.), WO 95/07723 (Wolf et al.), US Patent Application No. 2014/0000598 (Sutherland), WO 2013/043063 (Sutherland) and WO 2015/030610 (Sutherland), all incorporated herein in their entirety.

Numerous adherence monitoring device devices on the market have been developed for pressurised metered dose inhalers (pMDI) (e.g., U.S. Patent Application No. 2014-0182584 by the present assignee; WO2014/004437 by Gecko Health Innovations) and various types of dry powder inhalers, such as Turbuhaler™ (e.g., U.S. Patent Application No. 20140182584 by the applicant) or Diskus™ inhalers (applicant's SmartDisk™), all incorporated herein in their entirety.

Numerous other adherence monitoring devices have been described in relation to various inhalers by the applicant, e.g., PCT/IB2017/050893, WO2017/051389, WO2016/111633, WO2016/043601, WO2015/174856, WO2015/133909, WO2015/030610, WO2013/043063, WO 2010/114392, US20100250280, U.S. Pat. No. 9,468,729 and NZ 540250, all incorporated herein in their entirety.

While the adherence monitoring devices go some way towards assisting the patients in informed self-management of their disease and have been shown to improve patient adherence and health outcomes, there is always a need to find a lower cost solution which will assist in making the adherence monitoring device technology available to a wider user base. It would also be advantageous to find a reliable dose detection system that provides one or more of the following:

1) Could be applied across a range of devices;
2) Does not rely on mechanical interaction with the medication delivery device;
3) Is miniaturised and can be readily included within an add-on adherence monitoring device housing or embedded (i.e., adherence monitoring) medication delivery device, irrespective of their shape or size;
4) Could be included in the add-on adherence monitoring device or embedded medication delivery device in a way which allows for a complete water-proof design of such a device.

The present invention is concerned with adherence monitoring devices (add-on or embedded) which use low cost inductive coil transducers to detect medication usage events.

Use of inductive transducers has been described in the art.

U.S. Pat. No. 6,651,651 describes the use of inductive displacement transducer to detect actuation of a pressurised metered dose inhaler (pMDI) inhaler. The application discusses 3 types of placement of the inductive coils to detect depression of a medication canister within the pMDI. In the first example, a coil is attached to the exterior of the inhaler housing, around the inhaler housing diameter. In the second example, the coil is positioned within the inhaler, around the spray stem support, though this is not a preferred placement, as the patent notes that the "positioning of the inductive coil exterior to the housing is advantageous since it eliminates the possibility that the presence of the coil will affect the airflow profile within the device". The third example shows an actuation indicating device which is a tubular sleeve which slides over the pMDI inhaler housing. The tubular sleeve is provided with an inductive element in the form of coil which is tightly wrapped around the sleeve.

U.S. Pat. No. 7,347,200 in FIG. 4b shows a pMDI inhaler with an electronic dose counter. The dose counter comprises an inductive coil carrying a low electrical current. As in U.S. Pat. No. 6,651,651, the coil is located on the support under the spray stem, within the interior of an pMDI inhaler. The coil forms part of an inductive displacement transducer such that the depression of the canister disturbs the magnetic field created by the flow of current in coil. Actuation of the inhaler can therefore be detected as a change in the oscillating frequency of the circuit by the dose counter unit.

WO2007/137991 discusses similar placements of the inductive coil as in U.S. Pat. No. 6,651,651.

The above prior art shares the same common problem. The inductive coils used in the prior art must be coiled to surround the area in which the disturbance of the magnetic field or change of the inductive signal is to be detected. Their construction uses a series of wound conductors, which must be wound and placed accurately in order to achieve accurate position measurement. Potentially, a significant number of coils must be wound in order to achieve strong electrical signals. This construction significantly limits the applicability of the prior art solutions.

Further problems with the prior art is that they are unable to detect false signal events caused by interferences to the inductive field such as from the presence of additional metal, magnetic fields and mechanical disturbances.

While prior art solutions contemplate use of flat or helical coils, in all instances the inductive coils must detect presence of a material capable of disturbing the magnetic field as it passes through the coil. This solution limits the application of the inductive transducer to medication delivery devices which contain components that lend themselves to being surrounded by an inductive coil, e.g. pMDIs with a circular cylinder, syringes or medication bottles.

However, the prior art solution is not suitable for other types of medication delivery devices or adherence monitoring devices which, because of their shape, mechanics or general design, do not allow for inclusion of an inductive coil around their parts.

The present invention utilises inductive transducers to detect medication usage events. Preferably, the inductive transducer includes inductive coil sensors which do not require placement of a coil around a specific feature of the medication delivery device or an adherence monitoring device. This solution makes them suitable for use in all types of adherence monitoring devices (add-on or embedded), not only those characterised by a cylindrical body surrounding a feature characterised by its ability to disturb a magnetic field created by the inductive coil. The inductive coil sensors can be applied to any flat or curved surfaces of, or included within, the housings of various adherence monitoring devices.

Object

It is an object of the present invention to provide an adherence monitoring device which goes some way towards addressing the aforementioned problems and difficulties, or which at the very least provides the public with a useful choice.

SUMMARY OF THE INVENTION

In a first broad form the present invention provides an adherence monitor for a medication delivery device. In this form the invention can provide an adherence monitoring device arranged to detect the occurrence of a medication usage event of a medication delivery device.

According to one aspect, of the present invention provides an adherence monitoring device arranged to detect the occurrence of a medication usage event of a medication delivery device, the adherence monitoring device including at least one sensor configured to detect a medication usage event, said sensor being in the form of an inductive coil sensor, and said inductive coil sensor including at least one inductive coil and at least one inductive controller.

According to a further aspect, the present invention provides an adherence monitoring device arranged to detect occurrence of a medication usage event of a medication delivery device, the adherence monitoring device including a housing, and
at least one inductive coil sensor which includes at least one inductive controller, at least two inductive coils including a first inductive coil coupled to the housing and a second inductive coil coupled to the housing,
the first inductive coil configured to exhibit a response to an inductive change and provide a first change signal in response to an inductive change, and
the second inductive coil configured to exhibit a response to the inductive change and provide a second change signal in response to the inductive change, and a processor configured to receive sensor data from the inductive controller representative of the first and second change signals provided by the first inductive coil and second inductive coil and to compare at least one characteristic of the first change signal and the second change signal to detect the occurrence of a medication usage event or a false triggering event.

According to another aspect, the present invention provides an adherence monitoring device, wherein the change signal of the first inductive coil and the change signal of the second inductive coil are compared to determine the identity of a type of medication usage event that has occurred.

According to another aspect, the present invention provides an adherence monitoring device, wherein the medication usage event may include one or more of attachment or removal of a medication delivery device to or from the adherence monitoring device; placement or removal of a medication container; opening or closing of a mouthpiece cap; medication delivery device priming; medication release, opening or closing of a mouthpiece cap; medication delivery device priming; medication release or medication delivery.

According to another aspect, the present invention provides an adherence monitoring device, wherein false triggering events include detection of external metal interference, external electromagnetic field interference or deflection of the housing.

According to another aspect, the present invention provides an adherence monitoring device, wherein the first inductive coil and second inductive coil are positioned at different locations of the housing.

According to another aspect, the present invention provides an adherence monitoring device, wherein the inductive change is a delivery based inductive change caused by a change in proximity of an electrically conductive material of the medication delivery device during a medication delivery event relative to the first inductive coil, and the processor is configured to determine the occurrence of the medication delivery event when the at least one characteristic of the second change signal is an attenuated characteristic compared to the at least one characteristic of the first change signal.

According to another aspect, the present invention provides an adherence monitoring device, wherein the medication delivery event includes one or more of opening or closing of a mouthpiece cap; medication delivery device priming; medication release or medication delivery.

According to another aspect, the present invention provides an adherence monitoring device, wherein a position at which the second inductive coil is coupled to the housing results in the second inductive coil exhibiting the attenuated characteristic in response to the delivery based inductive change.

According to another aspect of the present invention, there is provided an adherence monitoring device for a medication delivery device, wherein at least one inductive coil is placed over, or adjacent to, the signal change area, as defined herein.

According to another aspect, the present invention provides an adherence monitoring device, wherein at least one of the inductive coils are configured to sense an inductive change within said signal change area, during said medication usage event and produce a change signal.

According to another aspect, the present invention provides an adherence monitoring device, wherein the inductive change is caused by a change in the proximity of an electrically conductive material target within the medication delivery device.

According to another aspect, the present invention provides an adherence monitoring device, wherein no portion of the at least one inductive coil is coiled around any portion of the conductive material target within the medication delivery device.

According to another aspect, the present invention provides an adherence monitoring device wherein the centre of the face of the at least one inductive coil is positioned substantially parallel to the direction of the motion that causes inductive change.

According to another aspect, the present invention provides an adherence monitoring device wherein the centre of the face of the at least one inductive coil is positioned substantially perpendicular to the direction of the inductive change.

According to another aspect, the present invention provides an adherence monitoring device, wherein the at least one inductive controller is configured to receive the first change signal from the first inductive coil and the second change signal from the second inductive coil and convert the first and second change signals into digital sensor data.

According to another aspect, the present invention provides an adherence monitoring device, wherein at least one inductive coil is a flat coil.

According to another aspect, the present invention provides an adherence monitoring device, wherein at least one inductive coil is formed on a substrate, the substrate being included within or upon the housing.

According to another aspect, the present invention provides an adherence monitoring device, wherein the substrate is a flexible substrate.

According to another aspect, the present invention provides an adherence monitoring device, wherein the substrate is a printed circuit board or PCB.

According to another aspect, the present invention provides an adherence monitoring device, wherein the at least one inductive controller is also formed on or within the substrate.

According to another aspect, the present invention provides an adherence monitoring device for a medication inhaler further including a processor wherein the processor operatively receives sensor data from the at least one sensor.

According to another aspect, the present invention provides an adherence monitoring device for a medication inhaler further including a user interface in a form of audio or visual reminders.

According to another aspect, the present invention provides an adherence monitoring device for a medication inhaler further including an alert system, the alert system configured to send a signal to the user following detection of a predetermined event.

According to another aspect, the present invention provides an adherence monitoring device, wherein the housing is removable attached to the medication delivery device. For example, in some embodiments the adherence monitoring device can be provided as an add-on device which is attachable to the medication delivery device.

According to another aspect, the present invention provides an adherence monitoring device wherein the housing is integrated with at least a portion of the medication delivery device. For example, in some embodiments the adherence monitoring device can be embedded within the medication delivery device.

According to another aspect, the present invention provides a method of recording the occurrence of a medication usage event of a medication delivery device using an adherence monitoring device, characterised by the steps of:
  a. identifying at least one characteristic of a first change signal sourced from a first inductive coil of the adherence monitoring device in response to an instance of an inductive change and identifying at least one characteristic of a second change signal sourced from a second inductive coil of the adherence monitoring device in response to the same instance of inductive change;
  b. comparing the at least one characteristic of the first and second change signals to determine the occurrence and identity of a medication usage event or detect the occurrence of a false triggering event, and
  c. recording the occurrence of the identified medication usage event when no false triggering event is determined to have occurred.

According to another aspect, the present invention provides a method of recording occurrence of a medication delivery event of a medication delivery device using an adherence monitoring device, characterised by the steps of:
  a. identifying at least one characteristic of a first change signal sourced from a first inductive coil of the adherence monitoring device in response to an instance of inductive change and identifying at least one characteristic of a second change signal sourced from a second inductive coil of the adherence monitoring device in response to the same instance of inductive change;
  b. comparing the at least one characteristic of the first and second change signals to determine if the at least one characteristic of the second change signal is an attenuated characteristic, and
  c. recording the completion of a medication delivery event if the second change signal exhibits an attenuated characteristic.

According to another aspect, the present invention provides computer readable storage media storing computer executable instructions that when executed are configured to implement a method of recording medication usage events by executing the steps of:
  a. identifying at least one characteristic of a first change signal sourced from a first inductive coil of the adherence monitoring device in response to an instance of inductive change and identifying at least one characteristic of a second change signal sourced from a second inductive coil of the adherence monitoring device in response to the same instance of inductive change;
  b. comparing the at least one characteristic of the first and second change signals to determine the occurrence and identity of a medication usage event or detect the occurrence of a false triggering event, and
  c. recording the occurrence of the identified medication usage event when no false triggering event is determined to have occurred.

According to another aspect, the present invention provides computer readable storage media storing computer executable instructions that when executed are configured to implement a method of recording medication delivery events by executing the steps of:
  a. identifying at least one characteristic of a first change signal sourced from a first inductive coil of the adherence monitoring device in response to an instance of inductive change and identifying at least one characteristic of a second change signal sourced from a second inductive coil of the adherence monitoring device in response to the same instance of inductive change;
  b. comparing the at least one characteristic of the first and second change signals to determine if at least one characteristic of the second change signal is an attenuated characteristic, and c. recording the completion of a medication delivery event if the second change signal exhibits an attenuated character.

In various aspects the invention is arranged to provide an adherence monitoring device, in addition to a method of recording the occurrence of medication usage, and in particular medication delivery events. In further aspects the invention may also provide computer readable storage media used to store computer executable instructions configured to implement such methods. Reference will be made primarily throughout this specification to the invention being implemented as an adherence monitoring device for a medication delivery device, while those skilled in the art will appreciate that the invention has a scope wider than just the provision of such an apparatus.

Furthermore, the physical arrangement and implementation of such an adherence monitoring device may vary in different embodiments. In some instances the components of the invention may be integrally formed within a medication delivery device, potentially during the manufacture of such a delivery device. In yet other embodiments the housing of the invention's monitoring device may be configured for removable attachment to a separate medication delivery device. In such embodiments the invention may provide an add-on or aftermarket component to be combined with a medication delivery device.

The invention is arranged to detect the occurrence of at least one medication usage event and/or a false triggering event experienced by a medication delivery device. Such medication delivery devices preferably include at least one moving part which changes its position relative to various components of the invention during a medication usage event to be detected by the invention. The invention may assist in detecting and preferably recording information regarding the use of such medication delivery devices.

In preferred embodiments the invention may be used to detect the occurrence of one or more usage events experienced by a medication delivery device, of which medication delivery events are a subset. For example in various embodiments a medication delivery device may be reconfigured by user without necessarily delivering a medication to this user, allowing a distinction to be made between usage and delivery events. In a range of embodiments the invention may be used to detect the occurrence of such non-delivery usage events in addition to the occurrence of delivery events.

In various preferred embodiments the invention may monitor, detect or record the occurrence of medication usage events such as the attachment or removal of the medication delivery device to or from the adherence monitoring device, the insertion or removal of a medication container, and/or medication delivery events such as opening or closing of a mouthpiece, medication delivery device priming, medication release or medication delivery.

In preferred embodiments the invention may also be sensitive to or be able to detect the occurrence of false triggering events. These false events may also cause an inductive change which an inductive coil integrated into the invention responds to. Such false triggering events may be detected or identified by the invention to determine if a valid medication usage event, and preferably a medication delivery event has occurred. In various embodiments the invention may potentially be used to detect the occurrence of false triggering events and store information about these events in their own right. For example in various embodiments the invention may be used to detect the occurrence of false triggering events sourced from external metal interference, external electromagnetic field interference or deflection of the housing of either the adherence monitoring device or the medication delivery device itself.

In preferred embodiments an adherence monitoring device may include at least two inductive coils including a first inductive coil coupled to the housing and a second inductive coil, again coupled to the same housing. Reference in general throughout this specification will also be made to an adherence monitoring device provided by the invention including only a first inductive coil and a second inductive coil. However those skilled in the art will appreciate that in other alternative embodiments three or potentially more inductive coils may be provided and utilised in accordance with the methodology of the present invention. Reference to the provision of a first and second inductive coil in isolation should not be seen as limiting.

The inductive coils provided with the invention are configured to exhibit a response to an inductive change and provide a change signal in response to their exposure to this inductive change. In particular, the first inductive coil is configured to provide a first change signal, and the second inductive coil is configured to provide a second change signal. The inductive coils are preferably configured to exhibit different responses to the same inductive change, such that at least one characteristic of the first change signal and the second change signal is different, allowing a comparative assessment of the respective change signals they produce to determine if a medication usage event or false triggering event has occurred in association with a medication delivery device. Different medication usage events or forms of false triggering events can result in different forms of inductive change being experienced by the inductive coils provided by the invention and resulting signal characteristics.

In various aspects of the invention the adherence monitoring device can include a processor capable of executing computer executable instructions. Preferably this processor may receive sensor data delivered by the inductive controller receiving change signals from the first and second inductive coils, where the inductive controller converts these change signals into digital sensor data. This processor may run executable instructions to compare these change signals and detect the occurrence of medication usage events, medication delivery events or false triggering events.

Reference is made predominantly throughout this specification of the inductive controller and the processor being formed by two separate and distinct components. However those skilled in the art will appreciate that the individual functions performed by the inductive controller and the processor may be undertaken by a single component with suitable circuitry in a number of embodiments. For example in one possible embodiment a single processor or microprocessor may be used to execute the signal characteristic comparison instructions required of the invention in addition to performing the various supporting signal conversion functions completed by the inductive controller. Those skilled in the art will appreciate that a range of circuit designs and combinations of separation of components may be used to implement the invention in various embodiments.

In various preferred embodiments the processor may also be programmed to identify the occurrence of a range of different medication usage events or false triggering events and to record occurrence data in relation to same. For example, in some embodiments a calibration process may be run to measure characteristics of each of the change signals to allow for recognition of specific patterns which are correlated with specific medication usage events, medication delivery events in particular, and false triggering events. One skilled in the art will appreciate that various well-known signal processing and analysis techniques may be used to implement such functions in accordance with the present invention.

In various embodiments the first and second inductive coils of the monitoring device may be configured to produce different signal characteristic responses to the same inductive change. This variability may be implemented by providing different characteristics or configurations of each coil such as, for example:

providing different coil conductor lengths, diameters, materials or winding geometries,
  locating the coils at different positions on or within the housing
  applying a magnetic shielding material to portions of one or both coils, potentially at on different regions of each coil.

In preferred embodiments the inductive coils provided with the adherence monitoring device may be configured to exhibit different responses to an inductive change event caused by a medication delivery event—referred to herein as a delivery based inductive change. In various preferred embodiments a delivery based inductive change may be caused by a change in proximity of an electrically conductive material of the medication delivery device when it undergoes a medication delivery event. Such medication delivery events can result in a relative change in proximity of this electrically conductive material relative to the first inductive coil, the second inductive coil, or potentially both coils.

In various preferred embodiments the adherence monitoring device's second inductive coil may produce a change signal with at least one attenuated characteristic in response to a delivery based inductive change. In a range of embodiments the second inductive coil may preferably be configured to exhibit an approximately similar response to all other medication usage and false triggering events other than dispensing events. The occurrence of an attenuated characteristic in a change signal sourced from the second coil can then be used to indicate the occurrence of a dispensing event.

In a preferred embodiment the first inductive coil and the second inductive coil may be positioned at different locations of the housing, with the position selected for the second inductive coil resulting in this coil's change signal exhibiting an attenuated characteristic in response to delivery based inductive changes. In such embodiments the first coil may be position at a location which ensures that it does not exhibit such an attenuated characteristic in response to a delivery based inductive change. In further preferred embodiments the first coil may be said to be positioned over or adjacent to a signal change area associated with delivery based inductive change.

As indicated above additional aspects of the invention also encompass a method of recording the occurrence of medication usage events, and/or a method of recording the occurrence of medication delivery events. These various methods provided by the invention may be implemented through computer executable instructions run by the processor of the adherence monitoring device referenced above.

In preferred embodiments the processor may assess the sensor data it is provided which was generated from the first and second coil's change signals when experiencing the same instance of inductive change. This assessment may identify or measure at least one characteristic of the change signals for comparison. Those skilled in the art will appreciate that various signal characteristics may be assessed in a number of embodiments, including but not limited to maximum or minimum amplitudes, signal frequencies, amplitude rate of change, power spectrums, polarity, and/or durations or periods at particular amplitudes.

After identification—and potentially measurement—of the change signal characteristic or characteristics of interest the processor may execute one or more instructions to compare a characteristic of the two different change signals.

In various embodiments this comparison operation can be used to determine the occurrence and identity of the medication usage event or detect the occurrence of the false triggering event substantially as described above.

In further embodiments a comparison may specifically focus on the detection of medication delivery events and make a comparison to determine if the second inductive coil has provided a change signal with an attenuated characteristic.

The processor can then be programmed to execute one or more instructions to record the results obtained from this comparison. In various embodiments the processor may record the occurrence of the medication usage event it has identified through this comparison operation when no false triggering event is determined to have occurred. Furthermore, the processor may record the occurrence of a medication delivery events if the second change signal of the second coil exhibits an attenuated characteristic.

BRIEF DESCRIPTION OF THE DRAWINGS

Additional and further aspects of the present invention will be apparent to the reader from the following description of embodiments, given in by way of example only, with reference to the accompanying drawings in which:

FIG. 10A is a perspective view of a prior art inhaler as included in the U.S. Pat. No. 8,479,730 (in FIG. 5 of the prior art application) with mouthpiece cover on.

FIGS. 18A-F are plots showing comparison of change signals provided by a first and a second inductive coil in response to a series of inductive change events in an embodiment where the invention is configured to operate with a pMDI;

FIGS. 19A-D are plots showing comparison of change signals provided by a first and a second inductive coil in response to a series of inductive change events in an embodiment where the invention is configured to operate with a Respimat® inhaler; and FIGS. 20A-B are plots showing comparison of change signals provided by a first and a second inductive coil in response to examples of inductive change events in an embodiment where the invention is configured to operate with a Diskus® inhaler.

Figure 1:
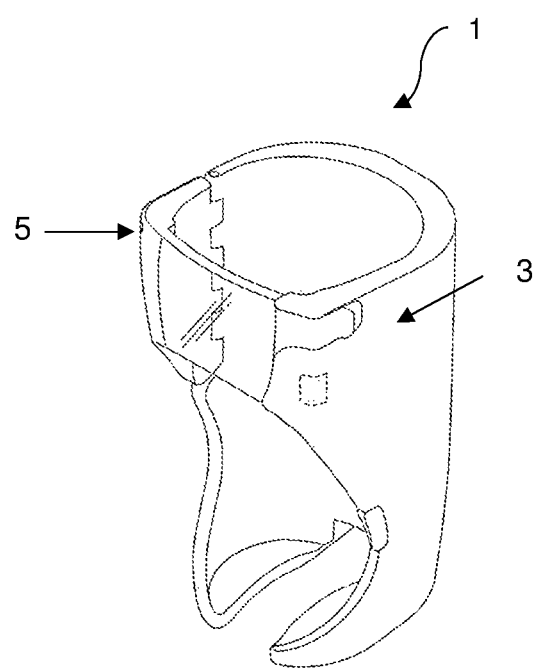
FIG. 1 is a perspective view of an adherence monitoring device of the present invention.

Further aspects of the invention will become apparent from the following description of the invention which is given by way of example only of particular embodiments.

DETAILED DESCRIPTION OF THE INVENTION

Throughout this specification, the terms "patient" or "user" or "person" or "patient usage", when used in relation to the use of a medication delivery device, are to be understood to refer to any person that uses a medication delivery device.

The present invention will be described in relation to various specific implementations, which it will be understood are intended to be illustrative and not limitative of the scope of the present invention. It will be appreciated in particular that various additional features and functions, indicators and the like may be included in monitors which implement the present invention. These may be selected for specific application at the option of the product designer.

The following implementations will be described with reference primarily to inhaler, in particular pressurized metered dose inhalers (pMDI), dry powder inhalers (DPIs), soft-mist inhalers, or capsule inhalers, as these are in widespread commercial use. However, the present invention may, with suitable modifications as will be apparent to those skilled in the art, be applied to other designs of inhalers, nebulisers or nasal sprays or any other medication delivery devices intended for delivery of inhaled medications. The general term inhaler will be used to refer to any such inhaled medication delivery device, unless a contrary intention is apparent from the context. Further, the present invention may, with suitable modifications as will be apparent to those skilled in the art, be applied to other medication delivery devices, in particular to any medication delivery devices which contain components capable of changing an inductive signal during a medication usage event (e.g., injection devices, injection pens, drips, etc.).

Similarly, whilst the discussion below is principally in relation to respiratory related medications, it is applicable to any use of medication dispensing inhaler devices, including, by way of example only, pain medication, diabetes, erectile dysfunction, or other conditions. The present invention is concerned with the monitoring of how the medication is used and dispensed, and should in no way be considered as limited to any particular medication or condition. The terms "medicine", "medicament" and "medication" should be broadly construed, and are not limited to any specific indication or types of inhalable substances. Further, the present invention is also applicable other types of medication, e.g., medication delivered orally or injected medication administered through a syringe, drip or any intradermal, subcutaneous, intramuscular, intravenous, intraosseous, intraperitoneal, intrathecal, epidural, intracardiac, intraarticular, intracavernous, and intravitreal infusion route.

The present invention is concerned with adherence monitoring devices which utilize inductive transducers to detect medication usage events. It will be appreciated that the present invention will be described with reference to implementations which are intended to be supplied as a device to be used over many replacement medication delivery devices, attaching to one and then removing when the medication delivery device is no longer used, for attachment to a new medication delivery device. It could be sold as part of or attached to a medication delivery device and removed for attachment to another medication delivery device. However, the present invention may also be implemented as an integral part of a medication delivery device (i.e., an embedded medication delivery device). It could be sold as a medication delivery device with an embedded adherence monitoring functionality and disposed together with the medication delivery device.

As a general explanation, the implementations of an adherence monitoring device described are intended to be used with a medication delivery device. The devices include systems to detect that a dose has been dispensed, and to retain or communicate a record of this to a remote system, for example via Bluetooth® to a smartphone, tablet or other device. The adherence monitoring devices of the present invention, together with firmware, software, databases and user interface automatically create a record of usage, to assist in clinical management and to provide remote user interface to enable patients to better manage their medication compliance. The adherence monitoring devices may also provide reminders to the user, detect whether or not a medication dispensing device is attached, provide error indications, or provide other functions.

Inhaled medication is often used in the treatment of respiratory diseases such as asthma, COPD, cystic fibrosis, and bronchiectasis. However, inhaled medication may also be used for the treatment of pain, heart conditions, erectile dysfunction, diabetes, and other indications. Inhaled medication is delivered via various forms of medication delivery devices, for example, inhaler, nebulisers, nasal sprays. Inhalers can take various forms.

A common type of medication inhaler is what is known as a pressurised metered dose inhaler (pMDI). Such inhalers generally comprise a medication canister and an actuator. The medication canister contains medication under pressure and is designed to deliver a metered dose of medication in the form of an aerosol spray. The actuator comprises a generally L-shaped hollow tube which has a first open end adapted to receive the medication canister, and a second open end which acts as a mouthpiece. The mouthpiece is often fitted with a removable cap.

Another type of medication inhaler is a dry powder inhaler (DPI). A common type of dry powder inhaler is in the form of a generally tube-shaped body (e.g. a TURBUHALER® which is manufactured and marketed by AstraZeneca AB), which includes an internal store of a suitable medication; a rotatable base for dispensing a single dose of the medication into an appropriate inhalation chamber; and a mouthpiece, through which a user may inhale the medication that has been dispensed into the inhalation chamber. Such dry powder inhalers usually come with a removable and replaceable screw-cap, adapted to cover the mouthpiece and tube-shaped body of the inhaler, when the inhaler is not in use.

Another common type of a DPI is in the form of a disc (e.g. GSK's Diskus® or Accuhaler® inhaler) which includes a priming lever, and the priming lever, when actuated, dispenses a metered dose of medication in the form of a dry powder into an appropriate receptacle adjacent a mouthpiece (which is usually covered by a cap when the DPI is not being used). The dry powder may then be inhaled by the user (namely, by sucking strongly on the mouthpiece of the inhaler).

Another type of medication inhaler is a breath-actuated inhaler (BAI). A BAI is in the form of a pMDI or a DPI in which the dose is delivered by a triggering mechanism internal to the inhaler in response to inspiratory flow rates exceeding certain pre-set levels, i.e. a patient's inhalation causes the dose to be delivered. An example of such a pMDI BAI is the Easi-Breathe® which is manufactured and marketed by Ivax/Teva.

Another type of DPI is an inhaler in which the medication is held within a capsule which is perforated by the user (e.g. by a use of a piercing button on the inhaler) prior to the inhalation during which the medication is delivered (e.g., HandiHaler® manufactured and marketed by Boehringer Ingelheim Pharma GmbH & Co. KG). Other types of DPI are also known (e.g. Genuair® by Almirall).

Another type of inhaler is a soft-mist spray (e.g. Respimat® Soft Mist Inhaler™).

Another type of DPI inhaler is ELLIPTA® (manufactured and marketed by GSK), and sold under a number of brand names: ANORO® ELLIPTA®, BREO® ELLIPTA®, INCRUSE® ELLIPTA®, RELVAR® ELLIPTA®. The ELLIPTA® DPI is described in a number of granted patents and patent applications, e.g., U.S. Pat. Nos. 8,161,968 and 8,746,242.

One example of a dry powder inhaler dispensing medication form a capsule is a Breezhaler™ (manufactured and marketed by Novartis AG), described in the U.S. Pat. No. 8,479,730. Another example is the HandiHaler® manufactured and marketed by Boehringer Ingelheim Pharma GmbH & Co. KG). Other types of DPI are also known (e.g. Genuair® by Almirall).

Another category of inhaled medication delivery devices are nebulizers which convert liquid medication into a fine mist which is breathed through a mask or a mouthpiece.

Another category of a medication delivery device is an injectable device, for example device described in PCT patent application publication WO/2001/095959 or WO2006/126902, incorporated herein by reference in their entirety.

The adherence monitoring devices of the present invention can use inductive transducers to detect medication usage events or false triggering events.

Preferably the inductive transducer used by the invention is an inductive coil sensor (ICS) consisting of at least one inductive coil and at least one inductive controller. The inductive sensor uses a magnetic field to detect the presence or proximity of electrically conductive objects.

The inductive coil may be a pickup coil, a magnetic loop sensor, an inductive proximity sensor, an inductive proximity switch, a magnetic reluctance sensor, an inductive charge coil, a sense coil, a charge coil, a communications coil or an antenna coil.

The inductive coil may be a wire, tape or any other electrical or magnetic conductive material formed into a coil. Inductive coils of any suitable type can be used: any conductive metal or other conductive material may be used. For example, inductive coil can be made from printed, painted or drawn conductive carbon tracks, printed in conductive ink, stamped metal (e.g., stamped aluminium foil), or copper. The inductive coil may take a form of a wound wire pancake coil.

The inductive coil may take different forms (coil, spiral, helix) and sizes depending on the shape, size and components of the medication delivery device or the adherence monitoring device. The coil may be a flat coil or may be a helical coil. Preferably the coil is a flat coil. Preferably, the size of the coil is determined by the distance between the coil and the component of the medication delivery device which is to be detected. Preferably, the coil diameter will be larger than the distance between the 'face' coil of a flat coil and the component to be detected. Preferably the coil diameter will be at least 2 times the distance between the 'face' coil of a flat coil and the component to be detected, more preferably at least 10 times the distance. Preferably, the coil diameter will be approximately 3 times the distance between the 'face' coil of a flat coil and the component to be detected.

The inductive coil may be a flat coil formed onto a flexible substrate and the flexible substrate can be arranged to hug the body of the inhaler (inside or on the housing of the device). The inductive coil can be etched on the housing of the add-on adherence monitoring device or an embedded medication delivery device. The inductive coil may be embedded in a sticker placed on the medication, the medication delivery device or the adherence monitoring device. The inductive coil may be implemented on a rigid PCB, flexible PCB or a rigid-flex PCB. Preferably, the inductive coil is a miniaturised flat planar coil formed on a PCB or thin film. The inductive coil may be formed on a flex PCB from about 0.1 mm thickness. Preferably, the inductive coil is a copper coil formed on a rigid, flex or rigid-flex PCB.

In some embodiments the inductive coil sensor may be a low power induction touch sensor, for example an LDC2112 or LDC2114 sensor available from Texas Instruments (see http://www.ti.com/lit/ds/symlink/ldc2114.pdf), an Azoteq IQS624 sensor or a Microsemi LX3301A. Such touch sensors have traditionally been used for inductive touch applications such as on user interfaces. Such inductive touch sensors may be configured to continuously track to a base line over time such that an in-built algorithm automatically compensates for any slow change in the sensor output caused by environmental variations, e.g. temperature changes. Thus, in the presence of constant or relatively constant conditions (i.e. sitting in a stationary position) the sensor output will slowly decay back to baseline. These sensors may be configured to send an interrupt signal to the micro-controller of the electronics control module (ECM, described below) when the output signal is above a predetermined threshold. The inductive sensor also preferably enables the polarity of the sensor output to be configured such that different sensors may provide different or opposing polarity signals in response to an event.

The inductive coil may be placed directly on the surface of a medication delivery device. Alternatively, it may be placed within an embedded medication delivery device. Preferably, it is placed on or within a housing of an attachable add-on adherence monitoring device.

One or more inductive coils can be placed on the printed circuit board or PCB. In some arrangements at least one coil may be placed on each side of the PCB. The inductive coil can be placed on multiple layer PCBs with additional coils stacked vertically, horizontally or offset in relation to the PCB axis for detecting movement of the components of the medication delivery device.

In some embodiments at least one inductive coil is preferably placed over the signal change area. For the purpose of this application, a signal change area means any portion of the medication delivery device characterised by an inductive change caused by the movement of or change in the proximity of conductivity altering parts of medication delivery devices or conductive material target within the medication delivery device, such as buttons, springs, containers, cogs, levers, cartridges, canisters, medication strips, brackets, etc. For example, the signal change area is an area where the metallic inhaler canister changes distance with respect to the inductive coil during canister depression at the time of medication release. In other embodiments, the conductive material target may be a non-conductive material customised by the addition of a conductive label, conductive etching, conductive print or conductive element.

In some embodiments of the present invention, the inductive sensing system consists of preferably of at least two inductive coils. References made below to 'the coil' or 'the inductive coil' should be interpreted as relating to either or any coil used within the present invention.

Preferably, the inductive sensing system consists of an at least one inductive sensing controller and at least two inductive coils configured as follows:

(a) the first of the at least two inductive coils is positioned in a signal change area, such that a medicament usage event, e.g. actuation of the medication delivery device, causes the maximum possible change in the first coil; and (b) the second of the at least two inductive coils is positioned outside of the signal change area, such that the second coil is not strongly affected by the medication usage event, i.e. the conductive material which moves during the medication usage event does not substantially alter its exposure relative to the second inductive coil. In these circumstances, a change signal provided by this second coil can exhibit at least one attenuated characteristic in response to a delivery based inductive change when compared with the change signal provided by the first coils in response to the same delivery based inductive change. For example, the total amount of metal in proximity to the second coil remains substantially the same before and during the medication usage event (e.g., 60% coverage before actuation to 60% coverage during actuation).

Preferably, no portion of the inductive coil is coiled to surround any portion of the conductive material target. For example, the inductive coil is positioned such that the conductive material target is not moving through the coil, but it is moving (or changing shape, e.g., a spring) relative to the inductive coil. In some embodiments of the present invention, the centre of the face of the inductive coil can be positioned substantially parallel to the direction of the inductive change. In other embodiments of the present invention, the centre of the face of the inductive coil can be positioned substantially perpendicular to the direction of the inductive change. Other orientations of the face of the coil in relation to the direction of the inductive change are also possible. Preferably, the inductive coil is positioned such that the distance between the centre of the inductive coil and the conductive material target changes.

In addition, the inductive coil can be located remotely from the controller, allowing for selective inductive coil placement in the medicament delivery device.

The inductive coil sensor (ICS) includes a controller which may be a dedicated induction sense controller, integrated circuit, a processor or a microcontroller with suitable external electronic components. Preferably the controller incorporates filters and converts the signal from the inductive coil to a digital signal. In some embodiments the ICS and the ECM referenced below may also be implemented using a single processor with suitable support circuitry.

The controller may be incorporated into the PCB of the adherence monitoring device.

The controller may incorporate filters and convert the signal from the inductive coil to a digital signal. Various filters may be incorporated, for example filters to remove any false medication dose triggers. The controller may be programmed to give a digital representation of how far away the inductive coil is from an object, and the filters will be programmed to filter out signals based on the amplitude, duration or the frequency of the signal. In some versions the inductive coil controller may include a baseline tracking function for the sensed inductive coil signal such that the baseline signal returns to a set baseline over time.

Preferably the ICS includes a multi-channel low-noise inductance-to-digital converter. Preferably, the ICS includes an LC resonator that offers high rejection of noise and interference. The ICS may be configured to detect small changes in the proximity of a conductive material target in relation to the inductive coil. The detection parameters depend on the size of the inductive coil, distance between the inductive coil and the target and the characteristics of the target, such as, for example, its size, shape or conductivity. The ICS may be configured to detect changes in the proximity of a conductive material target of about 200 nm at less than 1 mm from the inductive coil. Preferably, the ICS may be configured to detect changes in the proximity of targets of less than 200 nm.

Preferably, the ICS is an inductance-to-digital converter (LDC) sensor designed for inductive touch solution for low-power human machine interface button applications (such as http://www.ti.com/lit/ds/symlink/ldc2114.pdf or http://www.ti.com/product/LDC2112 by Texas Instruments). Inductive sensing technology enables touch button design for human machine interface (HMI) on a wide variety of materials such as metal, glass, plastic, and wood, by measuring small deflections or changes of proximity of conductive targets. The sensor for an inductive touch system is a coil that can be implemented on a small PCB located behind the panel and protected from the environment. Such an inductive sensing solution is insensitive to humidity or non-conductive contaminants such as oil and dirt. While the above LDC sensor is designed for use in touch button solutions, its size and flexibility makes it particularly useful for usage in detection of inductive changes caused by movement of parts or components of medication delivery devices, such as springs, containers, cogs, levers, cartridges, brackets, etc.

Preferably the ICS detects changes in the oscillating frequency to determine if there has been a change in the proximity of any components of the medication delivery device capable of disturbing the magnetic field created by the flow of electric current in the inductive coil. The ICS may also be used to measure how long an oscillating signal takes to decay, wherein the decay period can also be used to sense a change in inductance.

The ICS in the present invention is adapted to measure oscillating frequency shifts and determine when a medication usage event has occurred. A medication usage event is any event related to a medication delivery device, for example and without limitation: attachment or removal of a medication delivery device to or from the adherence monitoring device; placement or removal of a medication container (e.g., cartridge, syringe, capsule, canister, blister pack in or from the medication delivery device); opening or closing of a mouthpiece cap; medication delivery device priming (e.g., movement of a lever, turning of a portions of medication delivery device); medication release (e.g., compression or release of a button, movement of a lever, depression of a canister or a plunger); or medication delivery.

The ICS can detect inductive signal change caused by the movement of any component of the medication delivery device comprised of a material capable of disturbing the magnetic field created by the flow of electric current in the one or more inductive coil. For example, the component may be comprised of a magnetic or electrically conductive material such as stainless steel, copper, ferrite compound, aluminium, or alternatively the non-conductive component may have attached thereto a magnetic or electrically conductive component. The component may, for example, be a ring of material such as a ferrite ring or the component may be a coating or covering of suitable material. Alternatively, the non-conductive component may be modified by marking with conductive ink, e.g., tagged plastic part.

The ICS uses an inductive element to measure the position of the medication container relative to the adherence monitor housing. Since the inductive displacement transducer measures the relative proximity of the container to the housing it may also be thought of as an inductive proximity detector.

In some instances, the ICS will operate in the constant proximity of metal objects (canister) and baseline recognition would therefore be included in the firmware.

The ICS may be adapted to detect signal change triggered by the change in the distance between a specific component of the medication delivery device and the inductive coil.

Apart from the distance changes, the ICS may be programmed to detect changes in material type (metal A to metal B) or material density. The ICS can also be used to calculate the velocity and acceleration of a medication delivery device component, e.g., an inhaler canister moving down/up by, sampling detected values over time. This could be useful to filter out valid medication delivery device (e.g., inhaler) use from environmental noise. In other embodiments, the ICS may detect movement of any metalized plastic parts or metalized labels. In yet further embodiments, where ICs are placed on multiple sides and heights near the metal object it could detect swing/vibration of a component of the medication delivery device in 3D space.

Some state change signals from ICS may be used to power up a processor or ECM (defined below) of the adherence monitoring device.

Multiple coils may be used in devices to detect movement of metal parts and the direction of the movement of a component of the medication delivery device. For example, as it is illustrated below in relation to the SmartDisk™ adherence monitoring device shown in FIGS. 6A, 6B and 7.

The ICS can be fully incorporated into or embedded in the medication delivery device housing or in the add-on adherence monitoring device housing.

The use of ICS described in this invention removes the need for mechanical sensors which require physical contact with moving parts of the inhaler. The ICS sensor is capable of detecting various medication usage events through the medication delivery device housing or through the add-on adherence monitoring device housing. In contrast to pressure sensors the ICS does not require openings or channels to detect medication usage events. In contrast to mechanical or electromechanical sensors, the ICS does not require any mechanical stimulus from any component of the medication delivery device. This approach greatly simplifies design of watertight medication delivery devices or watertight adherence monitoring devices. This feature is particularly useful where the ICS is incorporated into the add-on adherence monitoring device.

The ICS is programmed to filter environmental factors and distinguish baseline signal and the desired medication usage event signal. For example, the ICS may be programmed to distinguish a dose delivery event from replacement of an inhaler in the add-on adherence monitoring device. This can be achieved via, for example, the signal from an "inhaler-in" sensor (e.g. an optical signal) providing a power up signal to the ICS. The power supply to the ICS will be controlled by a processor or ECM, for example, the power supply to the ECM may be connected following a signal form an accelerometer indicative of the medication delivery device being handled by the user.

Multiple coils may be used to prevent false triggering, e.g., a ring on user's finger on one side of the device will not set off the signal change and dose log. For example, by correlating the change on both sides of the medication delivery device, it is possible to determine if an external influence has occurred on one side of the medication delivery device only.

In some implementations of the present invention, the inductive coil may be shielded from external influences by adding a conductive or shielding material on the outer side of the coil (adjacent the outer surface of the device). The outer side of the coil being the opposite side to the side of the coil facing the signal change area, thus limiting the magnetic field dispersed outside the signal change area. The conductive or shielding material may include a ferrite material, a metal material, powdered metal material or carbon material.

The benefits of using ICS for detection of medication usage events or false triggering events include: low power use which is particularly important for non-rechargeable devices, low cost of sensors which is important to ensure affordability and wider distribution of the adherence monitoring devices. Unlike other sensors, inductive sensors are much less affected by foreign matter such as water, grease or dirt. Further, the ICS can be used for multi-purposes: same sensor can be used for multiple functions: the ICS can be employed to detect for example and without limitation, opening of a mouthpiece, priming of medication, medication release, medication delivery, removal or replacement of medication container, closing of a mouthpiece, etc. The ICS can further be employed to detect occurrence of false triggering events sourced from external metal interference, external electromagnetic field interference or deflection of the housing of either the adherence monitoring device or the medication delivery device itself.

In other embodiments of the present invention, the inductive coil described above may also be used as a wireless charging coil to charge a battery supplying power to the processor or ECM (as described below) or communications antenna for transmitting and receiving data relating to medication usage events or other information relating to the adherence monitoring device.

The adherence monitoring device of the present invention includes a processor configured to execute computer executable instructions to implement the methodology of the invention in various embodiments. This processor is referenced below as the electronics control module (ECM), with the ECM being adapted to monitor and/or manipulate and/or store and/or transmit all adherence data gathered, relating to the patient usage of the medication delivery device. The ECM may be implemented by any suitable microprocessor device.

The use of ECM, in conjunction with adherence monitoring devices for medication delivery devices, is well known, and it is not intended therefore to describe them in any significant detail herein. For example, these systems are in general terms in commercial use in products available from the present applicant and related companies, as well as disclosed in the applicant's prior patent filings, for example those incorporated by reference herein. An example of an adherence monitoring device, used in conjunction with an ECM and/or transmitter can be found in the applicant's U.S. Pat. No. 8,424,517 and US Patent Publication No. 2014/0000598, the contents of which are incorporated herein by reference in their entirety.

The ECM is powered by a battery, and either a rechargeable or replaceable battery may be used. The ECM and/or the adherence monitoring device may alternatively be powered by any suitable alternative means, for example a kinetic charger, by solar power, inductive charging or through harvesting power from ambient radio signals or light.

The ECM stores and transmits the adherence data gathered, so that analysis can determine if the user has used the medication delivery device correctly or incorrectly. The medication delivery device usage logs generated in the adherence monitoring device are uploaded into a smartphone application, a PC or a central communication hub, and through those into a web-based server. In some embodiments, the medication delivery device usage logs may also be uploaded from the adherence monitoring device directly into a web-based server.

Adherence monitoring device includes a memory. In some embodiments, a volatile type computer memory, including for example RAM, DRAM, SRAM, may be used. In such instances, the adherence monitoring device may continually transmit information to the computing device external to the adherence monitoring device or medication delivery device. In other embodiments non-volatile memory formats may be used, including for example ROM, EEPROM, flash memory, ferroelectric RAM (F-RAM), optical and magnetic computer memory storage devices, and others.

An add-on adherence monitoring device of the present invention may also include a sensor for detection whether the medication delivery device is attached to the adherence monitoring device. Sensors of this type have been previously described by the applicant. The sensor may be an IR optical sensor or a proximity sensor. Any other suitable sensor may be used. In some forms, the sensor may be located in an internal surface of the adherence monitoring device housing.

The adherence monitoring device may also include indication means, such as LED to indicate an event and/or to alert the user if the ECM determines that the user has used the medication delivery device correctly and/or incorrectly. The indication means may be utilised to alert the user if they have attempted to dispense a dose of medication with a mouthpiece cap still attached. Alternatively, the indication means may be used to alert if medication has not been dispensed within certain timeframe, e.g. every 12 h or 24 h.

The indication means may be in the form of one or more LEDs, or in the form of some other visual and/or audio and/or vibrational indicator. Adherence monitoring device also includes a multi-function user button for monitoring and controlling several aspects of operation. For example, pushing the button once may result in a green light showing if the adherence monitoring device is fitted to the medication delivery device correctly, and in normal working order. Conversely, a red light may indicate a problem. Pushing the button twice may provide for another aspect of the adherence monitoring device to be checked or reported, and furthermore pushing and holding the button may result in yet another function or check being done.

The adherence monitoring device of the present invention may also include a user interface enabling the user to access data recorded or received by the adherence monitoring device and also change the settings of the adherence monitoring device (for example, date/time, visual/audio alert settings). The user interface may also be used to access any data received (or transmitted) by the adherence monitoring device or to control the upload of the data from the adherence monitoring device to an external electronic device. The user interface may be located in the exterior surface of the housing of the adherence monitoring device.

The embodiments of the adherence monitoring device and/or the ECM described herein may be able to monitor for any type of non-dose counting information relating to the operation of the medication delivery device, and/or patient usage of the medication delivery device. For example, the ECM may include a real-time clock (or be in electronic communication with one) to enable the adherence monitoring device to record a date and time for each dose of medication dispensed. The ECM may be calibrated to compare the actual doses dispensed against the table of pre-set dosage times and, if the dose is not dispensed at the pre-set time, alert the user that a dose is due.

Furthermore, and for example only, the adherence monitoring device and/or the ECM may also be able to monitor criteria such as geographical location, temperature, humidity, the orientation of the medication delivery device, the condition of the medication, the amount of medication left, the condition of the battery or whether it is installed, the flow or pressure of the user's inhalation or medication flow in case of the injectable medication, an audio sensor for detecting inhalation or for determining if the main body portion has been rotated with respect to the base portion, or for detection of any other medication usage events. To this effect, the ECM may include an audio or optical inhalation sensor, thermistor sensor or accelerometer, or be connected to a GPS (e.g. the adherence data from the smartphone paired with the adherence monitoring device may be matched with the GPS data relating to the location of adherence events received by the smartphone).

An adherence monitoring device of the present invention may also include a communication device for transmitting the adherence data. In one embodiment, this may be a USB port located on the housing of the adherence monitoring device. Any other suitable wired connections or ports may be used.

Alternatively, and/or additionally, the adherence monitoring device and/or ECM may be provided with a wireless transmitter and/or a wireless transceiver e.g. Bluetooth Low Energy® module to be able to transmit and/or receive data respectively. Any other suitable wireless technology known in the art may be used, including for example Wi-Fi (IEEE 802.11), Bluetooth®, other radio frequencies, Infra-Red (IR), GSM, CDMA, GPRS, 3G, 4G, W-CDMA, EDGE or DCDMA200 or similar.

The data may be transmitted to a remote computer server or to an adjacent electronic device such as a smartphone or electronic tablet. The adherence monitoring device may be paired with a smartphone loaded with a software application which allows the smartphone to access, process, and/or present the data collected by the adherence monitoring device. The smartphone may be configured to transfer the data obtained from the adherence monitoring device to a web services platform. The data may be transmitted in real time, manually or at predetermined set times.

Figure 2:
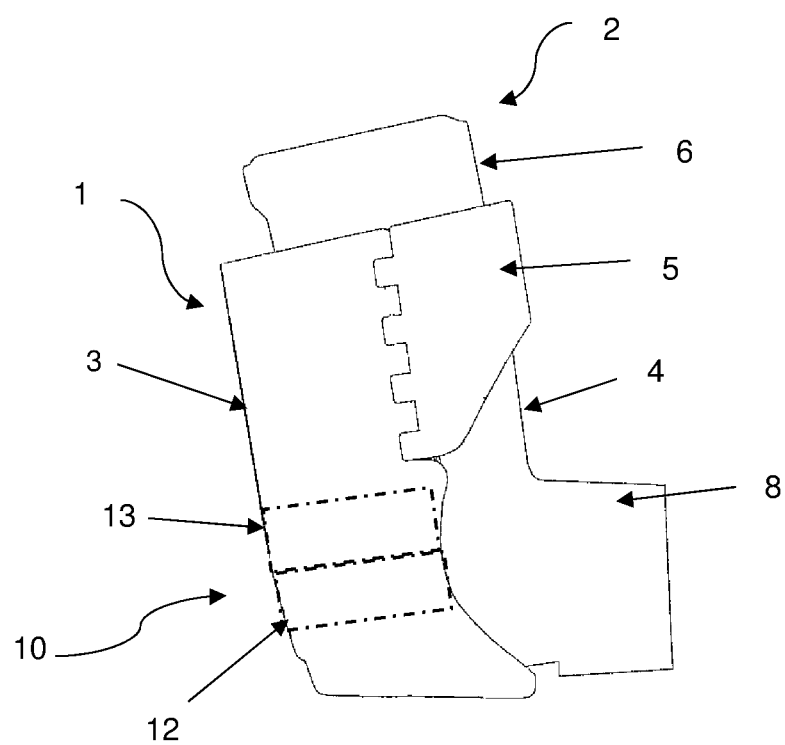
FIG. 2 is a planar view of the adherence monitoring device of FIG. 1.

Referring to FIGS. 1 and 2, there is shown an add-on adherence monitoring device 1 according to one implementation of the present invention. FIG. 2 shows the adherence monitoring device 1 attached to an existing medication delivery device or inhaler 2 (such as a Vannair® inhaler by AstraZeneca). The inhaler 2 includes an outer casing 4 and canister 6 which contains medication. The outer casing 4 of the inhaler 2 forms mouthpiece 8 for inhalation of the medication by the user. The adherence monitoring device 1 includes a housing 3 and hinged door 5 which allows the user to attach and remove the adherence monitoring device 1 to and from inhaler 2. The inductive coil sensor 10 is positioned on a rigid-flex PCB (not shown) held within the housing 3 of the adherence monitoring device 1. The inductive coil sensor 10 includes at least two inductive coils. The first of the at least two inductive coils is positioned anywhere within a possible signal change area 12 (indicated in dashed line). The second of the at least two inductive coils is positioned outside the signal change area. In some embodiments of the invention, the location indicated by arrow 10 may be the location of the inductive coils only, and the inductive controller portion of the ICS may be located in a different position, while maintaining communications with the inductive coils placed within the signal change area 12 and outside the signal change area 13. The second of the at least two inductive coils may be placed anywhere outsider the signal change area 12. Preferably, the second inductive coil may be placed as close to the first coil as possible to ensure other, non-medication events (e.g., false triggering events such as flex of the plastic walls of the adherence monitoring device, or interference from an external electrically conductive material) affects both coils the same way. Preferably, the second inductive coil may be placed so that it overlaps with the first coil while remaining outside the signal change area. Preferably the second inductive coil is coupled to the adherence monitoring device such that, in response to a delivery based inductive change (i.e., movement of the canister during an actuation), the second change signal provided by the second inductive coil exhibits at least one attenuated characteristic when compared with the first change signal provided by the first coil in response to the same delivery based inductive change.

Figure 3:
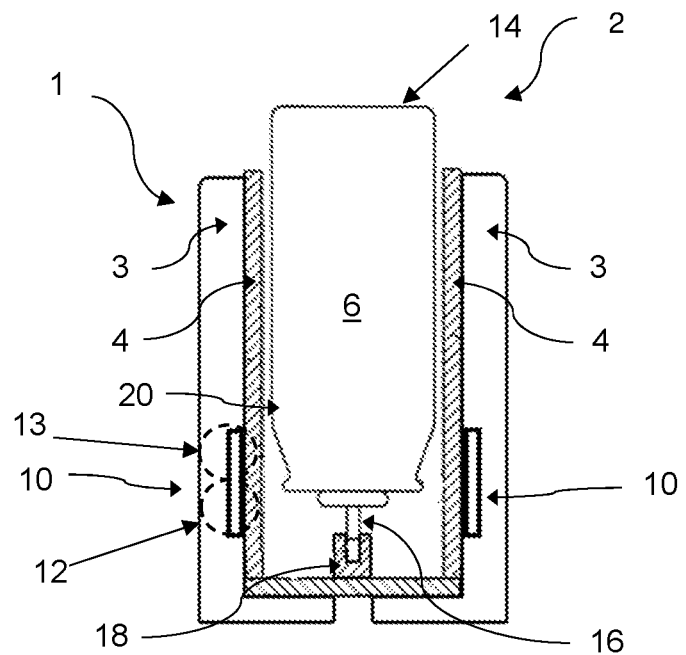
FIG. 3 is a cross-sectional view of another adherence monitoring device of the present invention attached to a pMDI, wherein the canister is not depressed.
Figure 4:
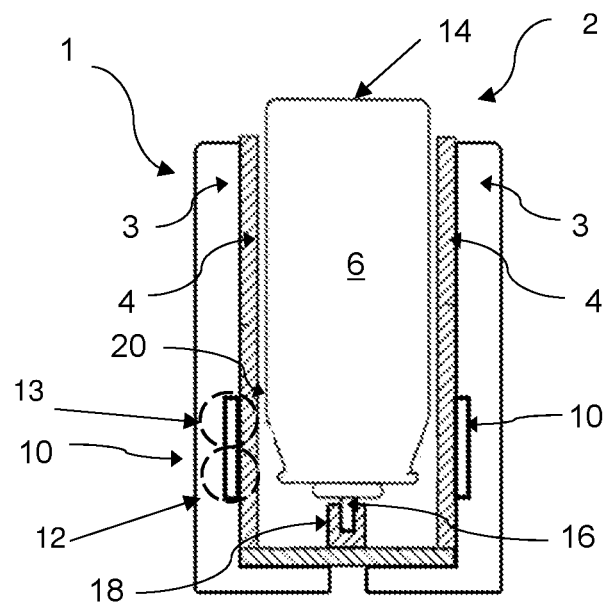
FIG. 4 is a cross-sectional view of the adherence monitoring device shown in FIG. 3, wherein the canister is depressed.

Referring to FIGS. 3 and 4, there is shown an add-on adherence monitoring device 1 according to another implementation of the present invention. The FIGS. 3 and 4 show a cross-sectional view of a pMDI inhaler wherein the inhaler 2 includes a spray stem 16, which is adapted to engage with the spray-directing element 18 formed integrally within the outer casing 4 of the inhaler 2. When the user dispenses a dose of medication, the user places their mouth over the mouthpiece (not shown) and presses down on the top 14 of the canister 6 to move the canister 6 from a rest position (shown in FIG. 3) to the dispensing position (shown in FIG. 4). This has the effect of pushing the spray stem 16 into the spray-directing element 18, which releases a metered dose of medication to the user. FIGS. 3 and 4 show two examples of possible locations of the ICS 10 within the housing 3 of the adherence monitoring device 1. Other locations of the ICS 10 are also possible. One or more ICS may be attached to the device 1. As above, in some embodiments, arrow 10 may indicate a location of an inductive coil only, with the inductive controller being placed in a different position within the adherence monitoring device 1 housing 3.

When the user presses the canister 6 down towards the spray-directing element 18, the inductive coil sensor 10 picks up the change in the proximity of the conductive object, in this implementation, the proximity of the canister 6 body 20 to the inductive coil sensor 10. The ICS 10 detects the canister 6 movement relative to the inductive coil within the ICS 10. The inductive coil is placed at the level of the canister neck (when inhaler 2 is in rest position) and when the canister 6 is pressed down to release a dose of the medication, the wider section of the canister body 20 slides past the inductive coil within the housing 3 of the adherence monitoring device 1 and the signal change is triggered within the ICS 10. The change signal is communicated to the ECM.

Any ICS 10 shown in FIGS. 3 and 4 may include at least two inductive coils. Arrow 12 indicates an example of the signal change area within which the first inductive coil may be placed. Arrow 13 indicates an example of the area outside the signal change area, where the second inductive coil is placed. In this embodiment the first inductive coil will produce a first change signal and the second inductive coil will produce a second change signal with at least one attenuated characteristic.

In embodiments where the ICS includes at least one coil in the signal change area and at least one coil outside the signal change area, the first coil is placed such that a medicament usage event, specifically a medication delivery event, such as depression of the medication canister, causes the maximum possible change in the first coil and a minimum change (if any) in the second coil placed outside the signal change area. This arrangement results in a second change signal with at least one attenuated characteristic as illustrated further in FIG. 18A.

The inductive sensing controller is preferably configured to output a positive value signal when a conductive object is placed in the proximity of the first coil and a negative value signal when a conductive object is placed above the second coil. As a consequence, when a conductive object is removed from the proximity of the first coil and the second coil, the inductive controller is configured to output a negative signal value from the first coil and a positive signal value from the second coil.

In this embodiment the configuration of the first coil and the second coil means that when a medication delivery device is actuated, there is an increase in signal value from the first coil and the signal value characteristic of the change signal from the second coil is attenuated.

The purpose of the second coil is to provide means for distinguishing between a medication usage event, such as an actuation, and a false triggering event, for example the user squeezing flexible walls of the adherence monitoring device 1. When a user applies enough force to the housing 3 of the adherence monitoring device 1, the plastic walls of the housing may deflect, essentially moving the first coil closer to the conductive material, leading to a first coil signal value similar to what is expected from a medication usage event. But, in this scenario of case deflection, the second coil will also move closer to the conductive material and will thus output a negative signal of magnitude similar to the magnitude of the positive signal output from the first coil.

The above false positive detection solution is particularly useful for adherence monitors constructed from flexible materials, which are susceptible to flex and movement of the housing of the adherence monitor. The two-coil solution can be applied to flexible PCBs, when flexible or rigid-flexible PCBs are required to fit with the design of an embedded medication delivery device or an add-on adherence monitoring device.

Preferably, the inductive sensing controller includes a built-in baseline tracking feature allowing the ICS to track any changes in the baseline signal and compensate for environmental changes. The changes may be nulled out continuously or under certain circumstances the baseline tracking may be disabled. Under certain circumstances, the baseline tracking may be immediately reset via software (for example step 312 in FIG. 13 and step 412 in FIG. 14).

The operating frequency of the ICS will be influenced by the type of the inductive transducer used. Preferably, the operating frequency of the ICS is between 1 MHz and 30 MHz. As a skilled addressee will understand the frequency range of the ICS will vary depending upon the type of inductive coil used as well as the number of coils within the sensor. It is understood that the frequency of the ICS is a factor of the inductance of the coil and the capacitance of the capacitor. The inductance of the coil is based on the number of turns, spacing between turns and the number of layers of the coil.

The sampling frequency of the ICS will be influenced by the type of power supply used in the adherence monitoring device 1 and the speed of the conductive component of the medication device being monitored. The sampling frequency is sufficient to ensure a triggering event is detected. For example, the sampling frequency may be between twice per second in a passive scanning (sleep) mode and 20 times a second in the active scanning mode, for example when the ICS is triggered into active scanning mode by a secondary sensor (an accelerometer or a switch). Preferably, the sampling frequency is between 5-10 times per second.

Figure 5A:
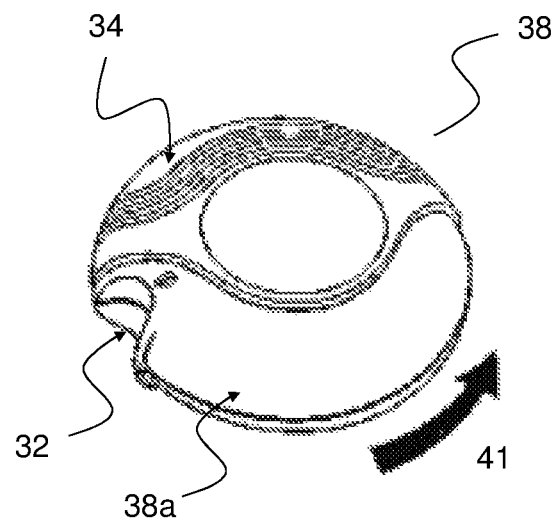
FIGS. 5A, 5B shows prior dry powder Diskus® type inhaler in a closed, non-dispensing position (5A) and open, dispensing position (5B)
Figure 5B:
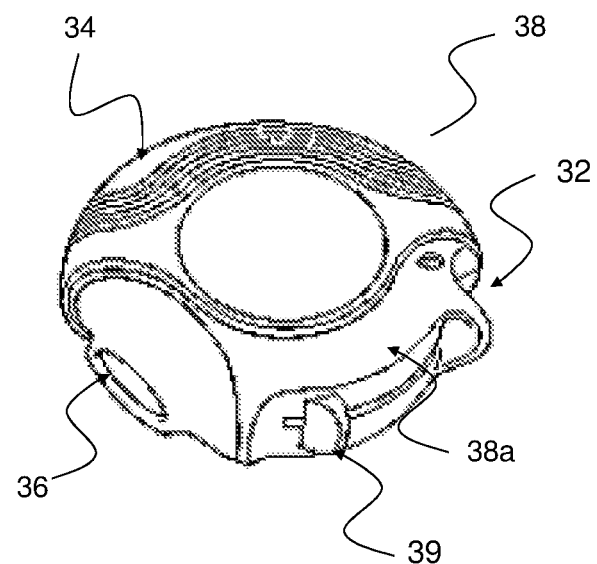
Figure 6A:
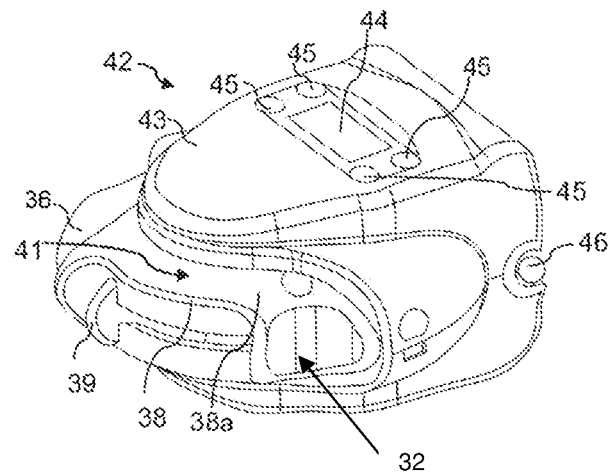
FIG. 6A is a perspective view of the adherence monitoring device of the present invention attached to a dry powder Diskus® type inhaler, where the inhaler is in a dispensing position.
Figure 6B:
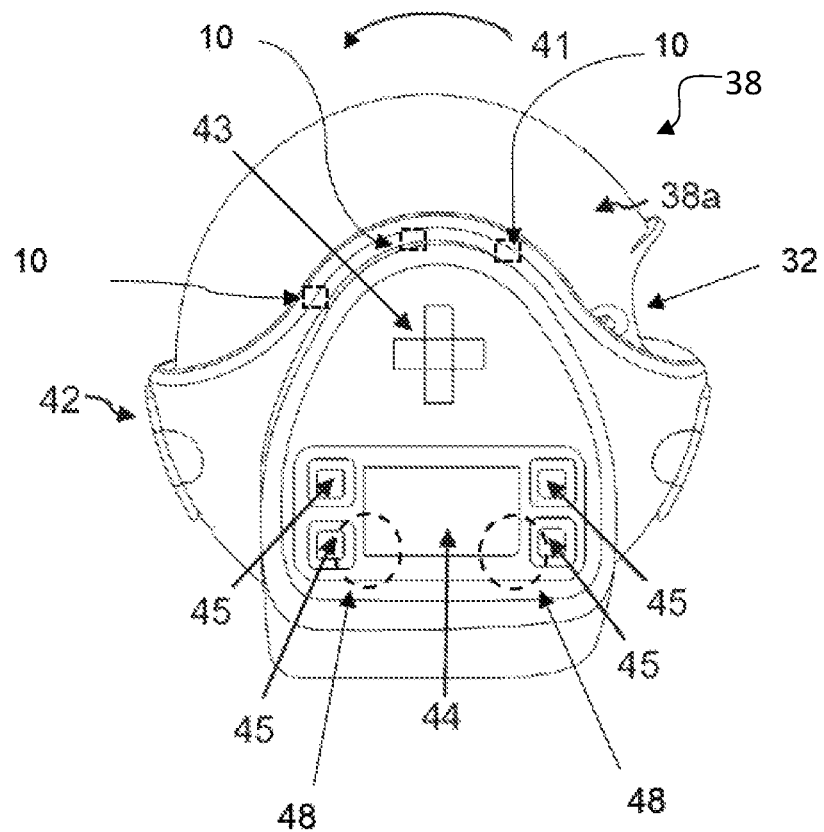
FIG. 6B is a planar view of the adherence monitoring device shown in FIG. 6A above with the inhaler in rest position.
Figure 7:
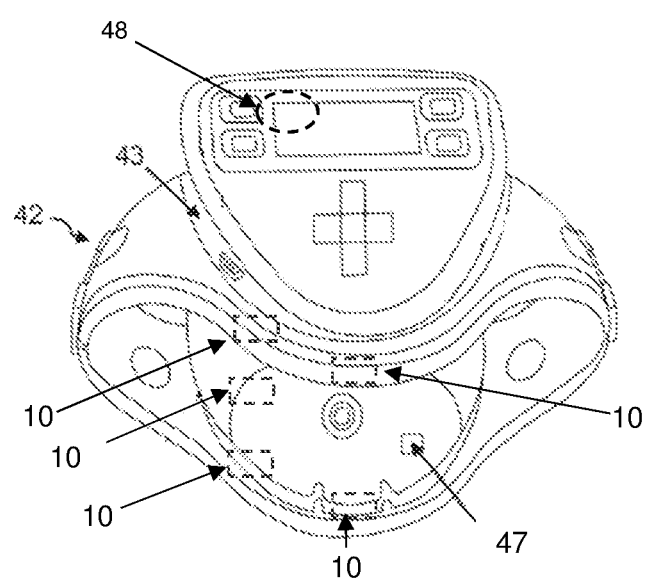
FIG. 7 is a perspective view of the adherence monitoring device shown in FIGS. 6A and 6B above with the inhaler removed.

Referring to FIGS. 6A, 6B and 7, there is shown an add-on adherence monitoring device according to another implementation of the present invention, for use with a known DPI inhaler in form of a disk (Accuhaler™ or Diskus™) shown in FIGS. 5A and 5B. The prior art DPI inhaler 38 is in the form of a disk which includes a store of dry powder contained in blister packs (not shown) coiled within the body 38a of the inhaler 38 and a mouthpiece cover 34. The body 38a of the inhaler 38 is inserted into or at least a portion is received within the mouthpiece cover 34. The prior art inhaler 38 includes a thumb grip 32, a mouthpiece 36 and a powder release lever 39. As a skilled addressee would understand the user rotates the portion 38a of the DPI inhaler 38, relative to the mouthpiece cover 34, using the thumb grip 32, from a closed (FIG. 5A) position to an open position (FIG. 5B) to reveal and provide access to the powder release lever 39 and the mouthpiece 36 to the user. In normal use, the lever 39 is moved in the direction indicated by arrow 41, and this releases a metered dose of dry powder into an internal cavity (not shown) adjacent the mouthpiece 36. The patient may then inhale the powder by sucking strongly through the mouthpiece 36. Prior art FIGS. 16a-16d of U.S. Pat. No. 5,860,419 show a DPI inhaler in the four successive stages of operation: closed position (16a), partially open position (16b), fully open position with actuation lever exposed (16c) and finally the dosing position (16d) with the mouthpiece fully open and lever in actuation position. The contents of this patent is incorporated herein by reference in its entirety.

Releasably attached to the inhaler 38 is an adherence monitoring device, generally indicated by arrow 42, for monitoring patient usage of the inhaler 38. FIG. 6B shows the DPI inhaler 38 in the closed position, where the mouthpiece 36 and the lever 39 are not accessible. To reveal the mouthpiece 36 and the lever 39, as shown in FIG. 5, the patient moves the portion 38a of the inhaler 38 in direction indicated by arrow 41, shown in FIG. 6B.

FIG. 6A shows an adherence monitoring device 42 attached to the DPI inhaler 38 and the inhaler 38 in the open position. The mouthpiece 36 and the lever 39 are accessible, and the user loads the medication by moving the lever 39 into the actuation position, by sliding it in the direction indicated by arrow 41.

The adherence monitoring device 42 includes a housing 43 which is substantially U-shaped and which is designed to slide over and fit snugly around a portion of the inhaler 38, generally around the mouthpiece cover 34. The housing 43 may optionally be provided with a hinge 46 to enable the housing 43 to hingedly open up into two halves in order to be fitted to the inhaler 38, if so desired or required. In other implementations of the invention, the housing 43 may be provided with a soft plastic or rubber portion to allow the user to push the inhaler 38 out of the housing 43.

Referring to FIG. 6B, the housing 43 includes an ICS (not shown) which is configured to determine medication usage events by detecting change in the oscillating frequency due to changes of the proximity of a conductive component of the inhaler 38 to the inductive coil located within the housing 43 of the adherence monitoring device 42. The change in the oscillating frequency within the coil is picked up by at least one inductive controller associated with the ICS. The ICS is further configured to detect false positive signals, i.e. change signals which are not in response to medication usage events, but inductive coil output changes caused by other, non-medication related events, such as false triggering events. Preferably the ICS includes at least one inductive coil placed in the signal change area (several examples are indicated by arrow 10) and one inductive coil placed outside the signal change area for example in location shown in dashed line and arrow 48. Preferably more than one inductive coil is placed in the signal change area along the curved edge of the housing 43 or in other locations within the housing 43, as shown indicated by dashed lines in FIGS. 6 and 7 and corresponding arrows 10. In some embodiments, the ICS may include at least two inductive coils placed within the signal change area. The coils may be placed within the housing 43 such the movement of conductive elements within inhaler 38 during a medication event affects the coils differently at different stages of the movement. The ICS may be configured to use the signals from such inductive coils to detect the direction of the movement of the inhaler or parts of the inhaler relative to the adherence monitoring devices 42. Preferably at least one first inductive coil is placed in a position indicated by arrow 10, within the signal change area and at least one second inductive coil is placed in the position within the housing indicated by the arrow 48. During the first medicament delivery event, i.e., opening of the mouthpiece 36, the first and the second inductive coils respond to the delivery based inductive change (as further illustrated in FIG. 20A). Due to its placement at position 48, the second inductive coil exhibits a delayed response to the delivery based inductive change. Conversely, as illustrated in FIG. 20B below, where the reverse situation occurs and the Diskus® inhaler mouthpiece cover 34 is replaced onto the mouthpiece 36, the second inductive coil exhibits the earlier response to the delivery based situation.

As some Diskus® type inhalers (described, for example, in U.S. Pat. No. 5,860,419, the contents of which is incorporated herein by reference it its entirety) contain no conductive components except the metal carrier strip for holding the medication in powder form, two or more inductive coils may be placed in positions allowing for detection of the spooling on or spooling off motion during the dose administration. Preferably multiple inductive coils are used to detect signal difference between the spools of peeled carrier strip or unpeeled carrier strip, enabling averaging or predicting when the blister medication is about to run out.

Having regard to FIG. 7, alternative positions of the inductive coils are illustrated by arrows 10. In some implementations, the inductive coils will be positioned in one location within housing 43 of the adherence monitoring device 42. In other implementations, the inductive coils may be positioned in several locations within the housing 43. The inductive coils may be positioned next to each other, substantially opposite each other or at different locations within the housing 43.

Preferably, the position of the inductive coils contained within the housing 43 of the adherence monitoring device 42 remains fixed relative to each other.

The adherence monitoring device 42 may also include at least one IR sensor 47 to detect the absence or presence of the inhaler 38 in the adherence monitoring device 42.

The device 42 also includes an electronic control module (not shown in FIGS. 5, 6 and 7). Furthermore, the housing 43 includes a user interface which includes an LCD screen 44 and operational buttons 45.

The device 42 only differs from the device 1 in its shape and design—in order for the device 42 to be able to fit a DPI inhaler 38 as compared to a pMDI inhaler 2. The device 42 may therefore have some or all of the same features and operational capabilities as the device 1 described previously in relation to the pMDI inhaler 2.

Other types of dry powder inhalers can also be monitored using the adherence monitoring device of this invention. For example, adherence monitors described by the applicants in PCT patent publications WO2016/043601, WO2015/133909 and WO2015/030610, the contents of which are incorporated herein by reference in their entirety, could be modified to include an ICS and additional conductive components in the rotor or the base of the adherence monitoring device, so that the rotational movement of the rotor in relation to the base could be detected by the ICS.

Referring to FIGS. 8A, 8B, 9A, 9B and 9C there is shown an add-on adherence monitoring device according to another implementation of the present invention. In particular, FIG. 8 shows schematic cross sections of the Respimat® inhaler, as included in the U.S. Pat. No. 8,387,614 (in FIGS. 1 and 2 of the prior art application).

Figure 8:
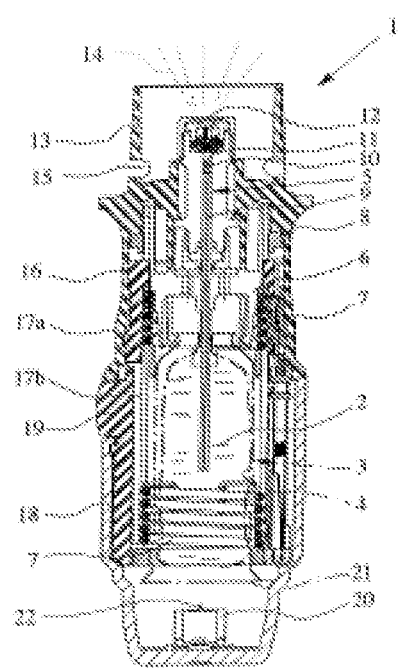
FIGS. 8A and 8B show prior art schematic cross-sections of the prior art Respimat® inhaler, as included in the U.S. Pat. No. 8,387,614 (in FIGS. 1 and 2 of the prior art application)
Figure 8:
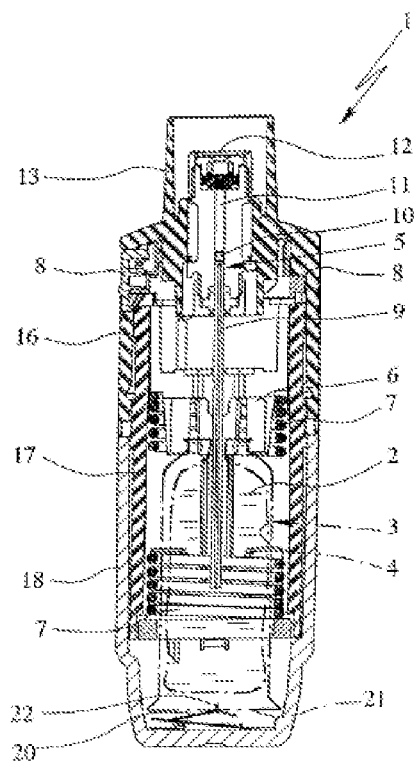

As illustrated by FIG. 8 (FIGS. 1 and 2 of the U.S. Pat. No. 8,387,614), during the administration of the medication from some embodiments of the Respimat® inhaler, the user rotates one housing part relative to another. This movement tensions a drive spring, which in turn moves the medication container held within the housing axially downwards until the container is pushed towards the base of the inhaler housing (as shown in the prior art FIG. 8B). During the atomisation process, the medication container is moved back by the drive spring to its starting position (as shown in the prior art FIG. 8A). The medication container performs a linear or stroke movement during the tensioning process and during the atomization process. When the drive spring is tensioned, the medication container moves with its end area further into the inhaler housing until the base of the medication container pushes down on a piercing element located on a working spring (folded spring) positioned on the inner wall of the base of the inhaler. The piercing element pierces the base of the medication container (or a seal in its base) during the initial contact for aeration. Following the initial contact, the piercing element remains in contact with the medication container or the container base, and therefore follows the linear or axial movement of the medication container until the medication container is removed from the inhaler and replaced with a new container.

Figure 9A:
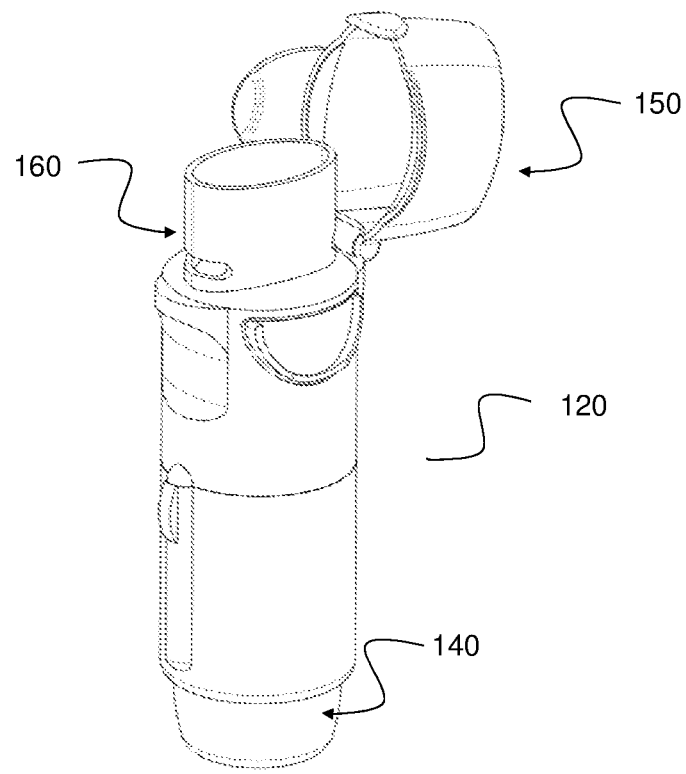
FIG. 9A is a perspective render view of a Respimat® inhaler alone, with the mouthpiece cover open and mouthpiece visible.
Figure 9B:
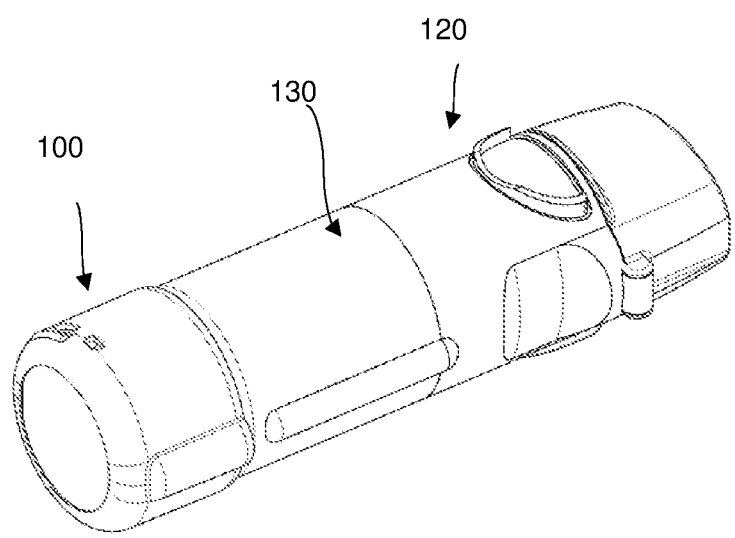
FIG. 9B is a perspective view of a Respimat® inhaler with another adherence monitoring device of the present invention attached to the base of the inhaler.

Referring to FIG. 9A there is shown a perspective render view of the Respimat™ Soft Mist inhaler 120 is shown, with the mouthpiece cover 150 removed and the mouthpiece 160 accessible. The same inhaler 120 is shown in FIG. 9B, with the mouthpiece cover 150 closed and another embodiment of the adherence monitoring device 100 of the present invention attached to the base 140 of the inhaler housing 130.

Figure 9C:
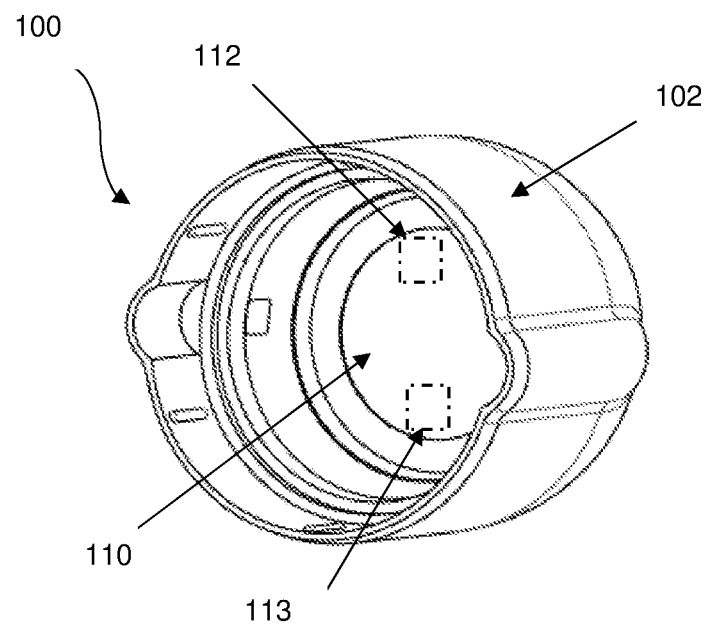
FIG. 9C is a perspective view of the adherence monitoring device shown in FIG. 9B, with the Respimat® inhaler removed.

FIG. 9C is a perspective view of another embodiment of the adherence monitoring device 100. The inductive coil sensor 110 is placed within the housing 102 of the adherence monitor device 100. The placement of the inductive coil is such that when the folded spring contained within in the base 140 of the inhaler 120 (as shown by arrow 20 in prior art FIGS. 8A and 8B) and the piercing element (as shown by arrow 22 in prior art FIGS. 8A and 8B) are pushed towards the base 140 of the housing 130 by the base of the medication container (as shown by arrow 21 in prior art FIGS. 8A and 8B), the ICS 110 detects the change in the proximity of the folded spring and triggers a change signal. Conversely, when the inhaler 120 is in the atomization process, the ICS 110 detects another change in the proximity of the folded spring (shown by arrow 20 in prior art FIGS. 8A and 8B) and also triggers a change signal. The ECM can be programmed to detect and characterize medication usage events based on the time lapsed between the two opposing signals.

The usage of the claimed invention in conjunction with the Respimat® inhaler 120 is similar to that of the previously described embodiments. One example of the ICS 110 is arbitrarily depicted as being positioned within the base of the housing 102 of the adherence monitoring device 100, but in other implementations of the present invention the ICS 110 may be positioned within the walls of the housing 102. Alternatively, as described earlier, the at least one inductive coil and the controller may be located in different portions of the adherence monitoring device 100. The adherence monitoring device 100 includes a housing 102 which can be substantially U-shaped, C-shaped, V-shaped, circular, rectangular, or of any other suitable geometry. This embodiment may partially enclose or fully enclose the inhaler 120. The housing 102 is designed to slide over and fit snugly around at least a substantial portion of the inhaler 120. The housing 102 can also be provided with a hinge to enable the housing 102 to open up into two halves in order to be fitted to the inhaler 120, if so desired or required. The inductive coil sensor 110 may be integrated into the housing 102 or on a surface of the housing 102 in any arbitrary manner, as long as the inductive coils have sufficient proximity to conductive components of the inhaler during medication usage events. For example, inductive coils may be based in the proximity of the folded spring or the piercing element when the adherence monitoring device 100 is attached to the inhaler 120.

Figure 9D:
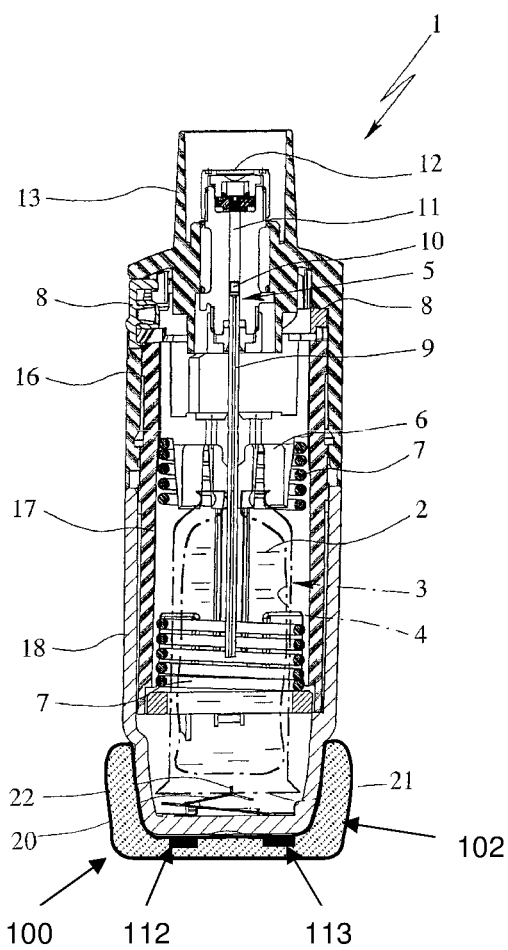
FIG. 9D shows the prior art figure shown in FIG. 8B, and a cross-sectional view of another monitoring device of the present invention attached to the base of the inhaler.

Preferably the ICS 110 includes at least one inductive controller and at least two inductive coils, where at least one inductive coil is located in the signal change area and at least one inductive coil is located outside the signal change area to produce an attenuated characteristic of the coil's change signal. As illustrated in FIG. 9D, inductive coils are preferably placed so that at least one inductive coil is positioned directly under the portion of the folded spring which moves with the movement of the medication canister (position 112)—the signal change area—and at least one inductive coil is placed directly under the non-moving portion of the folded spring (position 113), i.e. outside the signal change area. The first inductive coil positioned in the signal change area 112 is configured to be affected by the delivery based inductive changes caused by the change in proximity of the electrically conductive folded spring relative to the first coil. The second inductive coil placed in area 113 is configured to be less affected or not to be substantially affected by delivery based inductive changes and the changes in the proximity of the folded spring during medication delivery events. This configuration of the second inductive coil results in a change signal which exhibits at least one attenuated characteristic when compared to the first change signal from the first inductive coil.

Figure 10A:
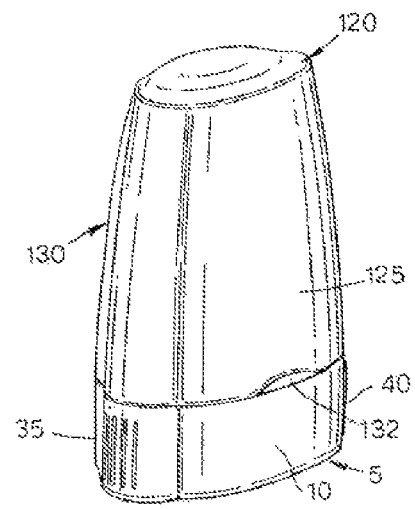
Figure 10B:
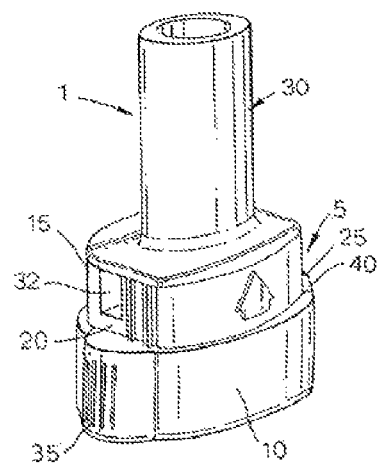
FIG. 10B is a perspective view of a prior art inhaler as included in the U.S. Pat. No. 8,479,730 (in FIG. 1 of the prior art application) with the mouthpiece cover removed.

Referring to prior art FIGS. 10A and 10B, there is shown a prior art Breezhaler® inhaler device (by Novartis) with mouthpiece cover on (10A) and off (10B), described in the U.S. Pat. No. 8,479,730, the contents of which is incorporated herein by reference in its entirety.

Referring to FIGS. 11A-D, there is shown an add-on adherence monitoring device 202 according to yet further implementation of the present invention, for use with an existing medication inhaler 201.

Figure 11A:
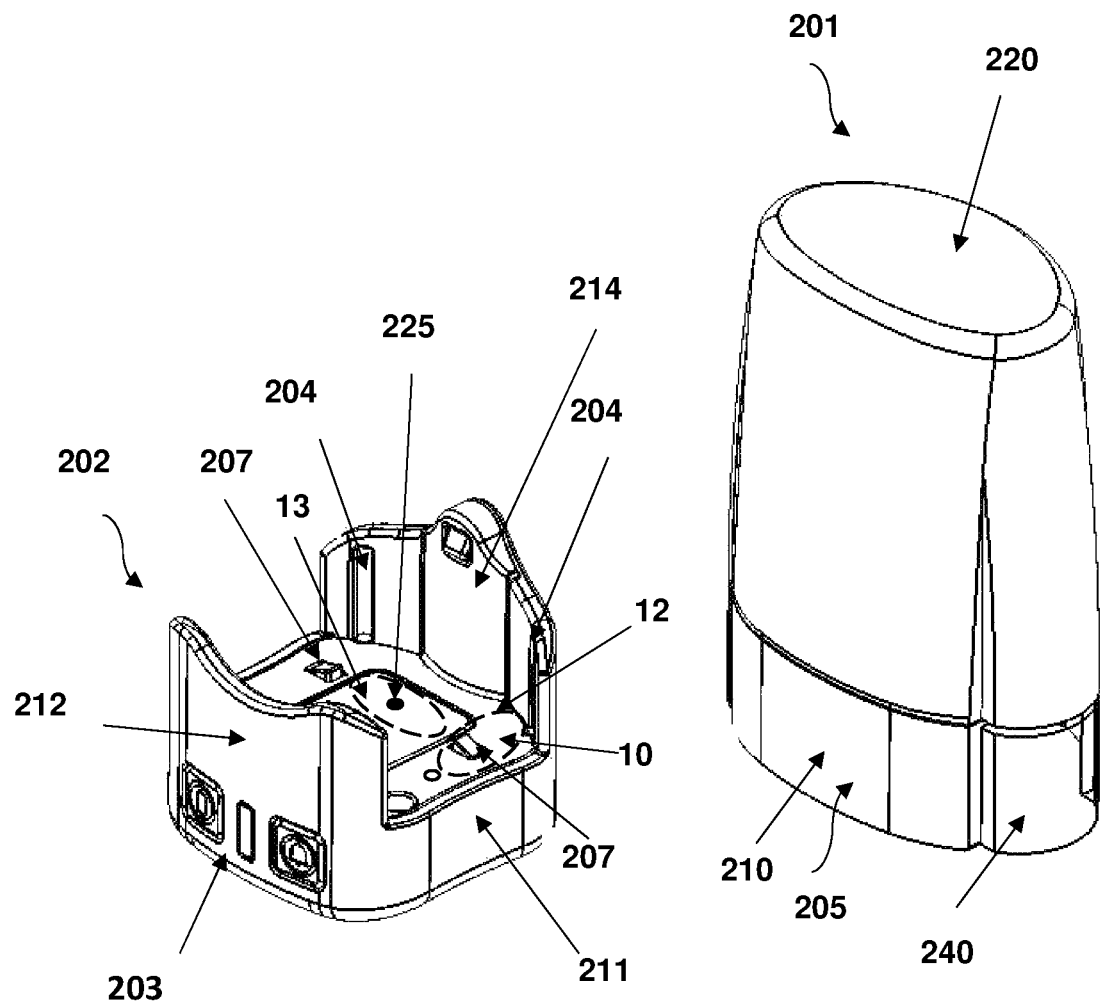
FIG. 11A is a perspective view of a Breezhaler® inhaler illustrated by FIGS. 10A, 10B and another adherence monitoring device of the present invention.
Figure 11B:
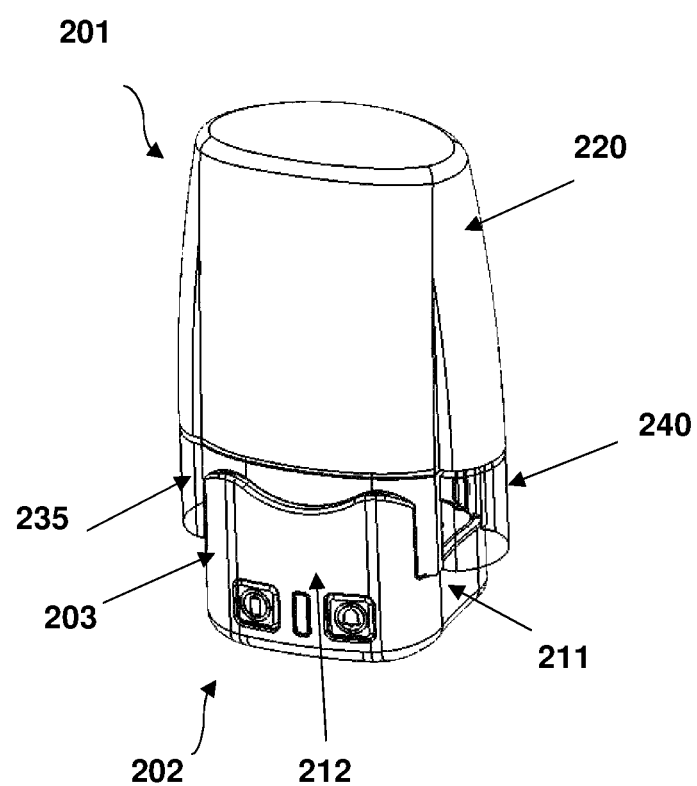
FIG. 11B is a perspective view of the adherence monitor shown in FIG. 11A, wherein the adherence monitoring device is attached to the Breezhaler® inhaler.
Figure 11C:
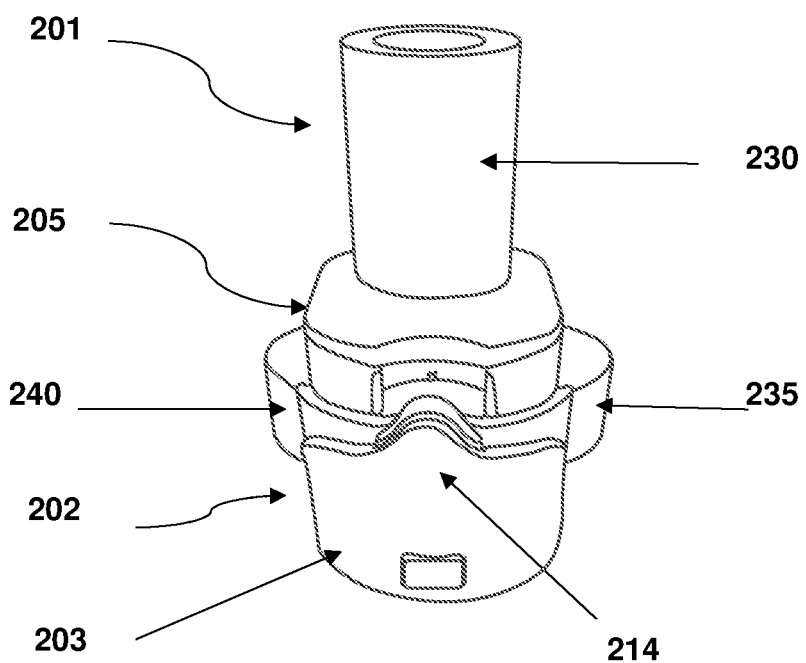
FIG. 11C shows the adherence monitor shown in FIG. 11A from a rear view with the adherence monitor attached to the Breezhaler® inhaler from which the cap has been removed.

FIGS. 11A-D show the inhaler device 201 which includes a body 205 and a cap 220. The cap 220 is removable, replaceable and adapted to close off the mouthpiece 230 when the inhaler 201 is not in use. The body 205 of the inhaler 201 includes a recess 250 for holding a capsule containing a powdered medication to be inhaled, a mouthpiece 230 that includes a coaxially disposed inhalation passage 270 that communicates with the recess of the body 205. The body 205 has a pair of opposed spring biased push-buttons 235 and 240 that each include at least one piercing element 260 for piercing the capsule when loaded into the recess. The medication is released from the pierced capsule when air is drawn through the air passage(s) 270 into the recess 250 and swirled about therein. The mouthpiece 230 is pivotally attached to the edge of the body 205 so that it is pivotable between an open loading position (FIG. 11D) and a closed dispensing position (FIG. 11C). In this example, in the closed dispensing position the mouthpiece 230 is in an upright or substantially vertical position. In the open loading position, the mouthpiece is in a substantially horizontal position. However, it is noted that in other forms the mouthpiece of the inhaler 201 may be configured to move in other directions or ways such as slide or swivel in a sideways direction (not shown).

To dispense the medication from the inhaler device 201, the user takes off the cap 220 from the mouthpiece 230, moves or pivots the mouthpiece 230 into an open position and places a capsule (not shown) containing a powdered medication to be administered into the capsule chamber 245 of the recess 250. The user then moves or pivots the mouthpiece 230 back to its closed position ready for dispensing the medication. The user pushes both push buttons 235 and 240 to activate a capsule piercing mechanism illustrated in FIGS. 12A and 12B. The mechanism comprises a pair of needles 260 that project inwardly from the push buttons 235 and 240 towards the recess 250. After the push buttons 235 and 240 have been compressed and the capsule pierced, the user releases the pressure on them and the buttons are urged outward by springs 265. Users administer the medication by breathing out fully, inserting the mouthpiece 230 into the mouth, placing their lips and teeth around the mouthpiece and inhaling quickly and deeply. This action draws surrounding air into the inhaler device 201 through the air inlets 232 along the air passages 270, and into the recess 250.

Referring to FIGS. 11A to 11D, there is further shown the inhaler device 201 and an adherence monitoring device 202 according to an embodiment of the present invention. The adherence monitoring device 202 is housed within a second housing 203, which is releasably attachable to the inhaler device 201. The second housing 203 is adapted to attach to the body 205 of the inhaler 201, gripping the front 210 and the back (not shown) of the inhaler 201, without interference with the operation of: the push buttons 235 and 240, the mouthpiece 230, the air inlets 232, or the pivotal movement of the mouthpiece to allow opening/closing and access to the recess 250.

In some embodiments, the second housing 203 may attach to the inhaler 201 by friction, mechanical coupling, adhesive coupling or other releasable coupling methods. Ensuring that the second housing 203 retains inhaler 201 securely without additional tools, adhesives or tape was an obstacle.

Figure 11D:
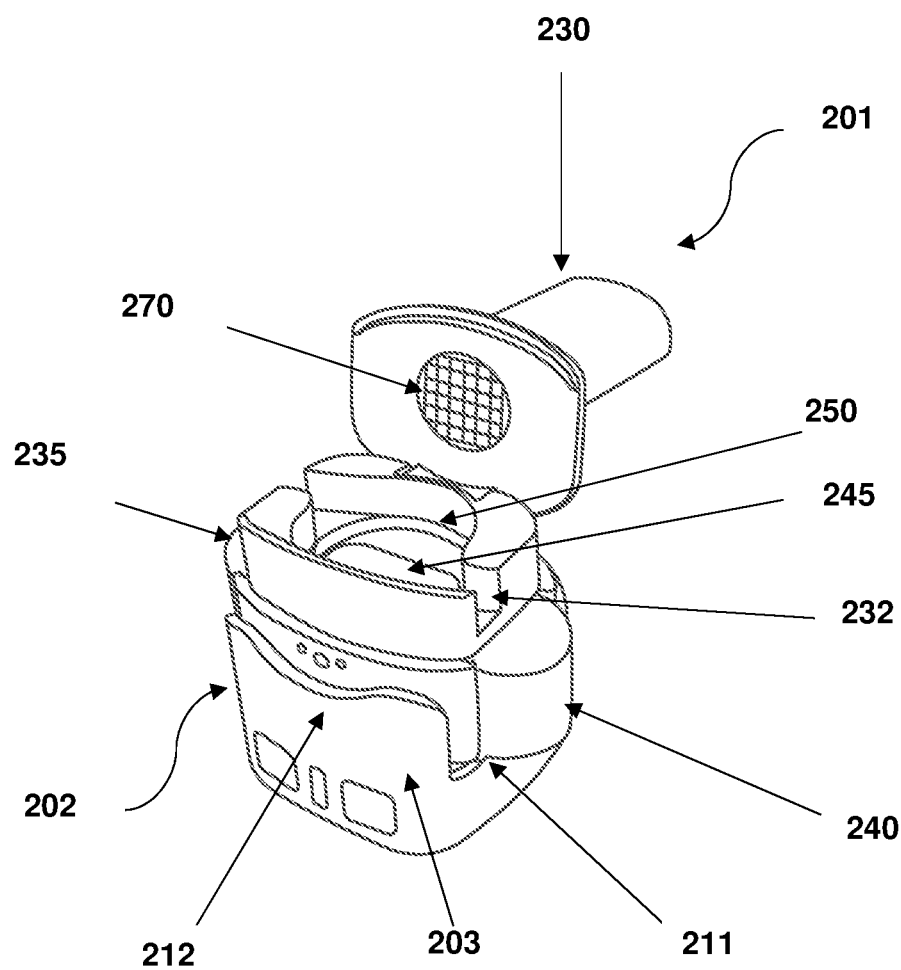
FIG. 11D shows the adherence monitor shown in FIG. 11A from a front view attached to the Breezhaler® inhaler, showing the cap removed and the inhaler mouthpiece fully opened to give access to the recess for holding the medicament capsule.

In some embodiments of the adherence monitoring device 202, as seen in FIGS. 11A-11B and 11D, the second housing 203 may include a bottom base 211 with an upright front and back walls 212, 214 extending therefrom. The inhaler 201 is inserted between the front wall 212 and back wall 214 and rests upon the bottom base 211 (see FIG. 11B). The front and back walls 212, 214 are preferably configured such that they will not impede the movement of the mouthpiece of the inhaler 201 in use. For example, the maximum height of the back wall 214 may be shaped to still allow the opening of the mouthpiece for insertion of a capsule of medication. The heights of the front wall 212 and the back wall 214 may be different as shown. Alternatively, the front and back walls may have similar heights (not shown). The front wall 212 and back wall 214 are configured to provide sufficient surface area in contact with the outer surface of the inhaler body 205 to retain the adherence monitoring device 202 on the inhaler 201.

In some embodiments one or more retainers 204 may be provided on the inner surface of the adherence monitoring device 202. In one embodiment there may be are four retainers 204, two provided on the front wall 212 and two on the back wall 214. To ensure secure yet releasable attachment seal elements (such as toroidal seal) may be bonded onto the front and back walls 212 and 214 respectively.

In other embodiments, the adherence monitoring device 202 may consist of two portions, such as front and back portions or two side portions, connected by a hinge and attachable to the inhaler device 201 by clamping them onto the body 205.

In other embodiments, the adherence monitoring device 202 may consist of at least two portions, such as front and back portions, which can be connected via an internal spring-loaded releasable catching latch and thus fitted around the body 205 of the inhaler device 201.

In other embodiments, the adherence monitoring device 202 may attached to the body 205 of the inhaler 201 using flexible, elastic material (not shown).

When fitted onto the inhaler 201 the adherence monitoring device 202 permits the user to dispense the medication as described above, without any interference with the cap 220, mouthpiece, air inlets, capsule recess, or push buttons 235 and 240.

The adherence monitoring device 202 shown in FIGS. 11A-11D may include a sensor 225 for detecting that the adherence monitoring device 202 is attached to the inhaler 201.

The sensor 225 may be a mechanical, electromechanical or electronic sensor. The sensor 225 may be an optical IR sensor that detects the presence or absence of the base or wall of the inhaler within a certain distance by generating data output based on optical signal received. The location of the sensor 225 as shown in FIG. 11A is indicative only and the sensor 225 may be in or on any other location of the adherence monitoring device 202 provided that the sensor 225 can detect when the inhaler 201 is inserted into the adherence monitor 202. Preferably the sensor 225 is provided within or on the base 211, front wall 212 or back wall 214.

In the embodiment illustrated in FIG. 11A the sensor 225 is an optical IR sensor that detects the presence of absence of the base or wall of the inhaler within certain distance by generating data output based on the optical signal received. The sensor 225 includes an infra-red light emitter and infra-red light receiver positioned in such way that the optical signal emitted from the emitter is reflected off the base or the wall of the medication inhaler and received by the receiver. The sensor 225 may be located in any position on or within the base 211, front walls 212 or back wall 214 provided that the optical signal emitted by the IR sensor is blocked or altered by the body of the inhaler 201 once it has been inserted into the adherence monitoring device 202. The data output of the receiver is processed by the processor to determine if the output is consistent with 'inhaler in' or 'inhaler out' parameters recorded in the memory database.

The adherence monitoring device 202 may include at least one dose preparation sensor 207 for detecting compression or release of the push buttons. In some forms the at least one dose preparation sensor 207 is a micro-switch and the adherence monitoring device 202 includes at least one micro-switch 207 to detect the compression or release of at least one of the push buttons 235, 240.

In one embodiment of the present invention, the sensor 225 or 207 may be replaced or assisted by the inductive coil sensor 10. The inductive coil sensor 10 is configured to detect the changes in the proximity of the springs 265 or the piercing needles 260 indicative of compression or release of at least one of the push buttons 235, 240. The inductive coil sensor 10 is further configured to detect changes in the proximity of any conductive material target within the inhaler 201 to the inductive coil associated with the ICS 10, where the change is indicative of the inhaler 201 being inserted in or removed from the adherence monitoring device 202. One example of the ICS 10 is arbitrarily depicted as being positioned within the base of the base 211 of the adherence monitoring device 202, but the ICS 10 may be positioned in any suitable signal change location within the base 211 or within the walls front wall 212 or back wall 214.

Figure 12A:
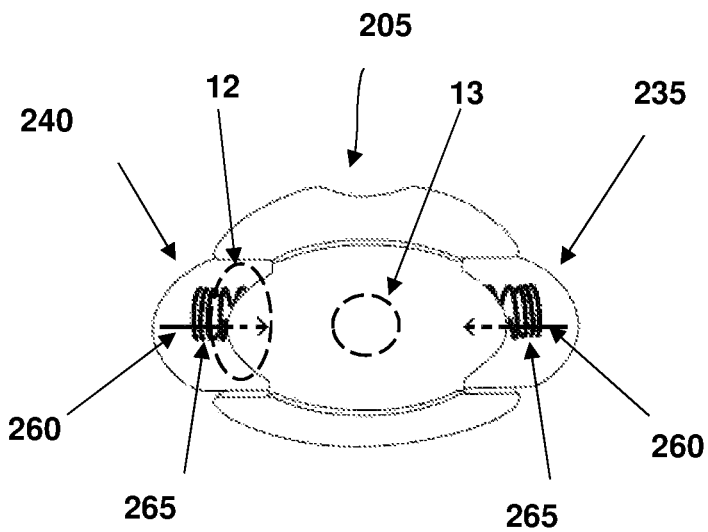
FIGS. 12A and 12B are planar views of the base of the Breezhaler® inhaler illustrating the movement of the springs and piercing elements during a medication usage event: before the piercing of the medicament capsule (12A) and with the push buttons compressed to pierce the medicament capsule (12B)
Figure 12B:
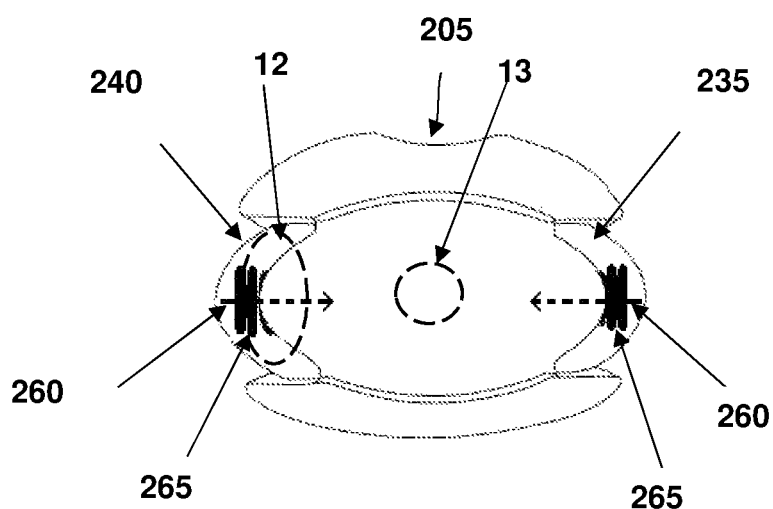

FIGS. 12A and 12B show views of the base of the inhaler 201 which illustrate the position of the push buttons 235 and 240 prior to the compression by the user (FIG. 12A) and at the point when the user pierces the capsule (FIG. 12B). When the user pushes the push buttons 235 and 240 inwardly towards the recess 250, the proximity of the springs 265 and piercing needles 260 included within the push buttons 235, 240 changes relative to at least one inductive coil placed in position 12, altering the oscillating frequency within the inductive element of the inductive coil sensor 10. The change in signal is logged as a compression of the push buttons 235 and 240 indicative of the medication usage event, i.e. preparation of the dose for inhalation.

Conversely, when the push buttons 235 and 240 are released they have the opposite effect on the ICS 10 and the inductive coil placed in position 12, as the conductive material of the spring 265 or piercing needles 260 is at least partially removed from the detection area of the inductive coil. The change in signal from the ICS 10 is logged as release of the push buttons 235 and 240.

Preferably, the ICS 10 of the adherence monitoring device 202 includes at least one inductive controller and at least two inductive coils, one placed within the signal change area, shown by the dashed line and arrow 12 (FIGS. 11A, 12A and 12B) and at least one inductive coil placed outside the signal change area, for example, in the area indicated by the dashed lines and arrow 13 (FIGS. 11A, 12A and 12B). The inductive coil in the signal change area 12 will be affected by the changes in the proximity of springs or the piercing needles. The inductive coil placed in area 13, is configured not to be strongly affected or not to be substantially affected by medication dispensing events. This configuration of the second inductive coil results in a change signal which exhibits at least one attenuated characteristic.

Figure 13:
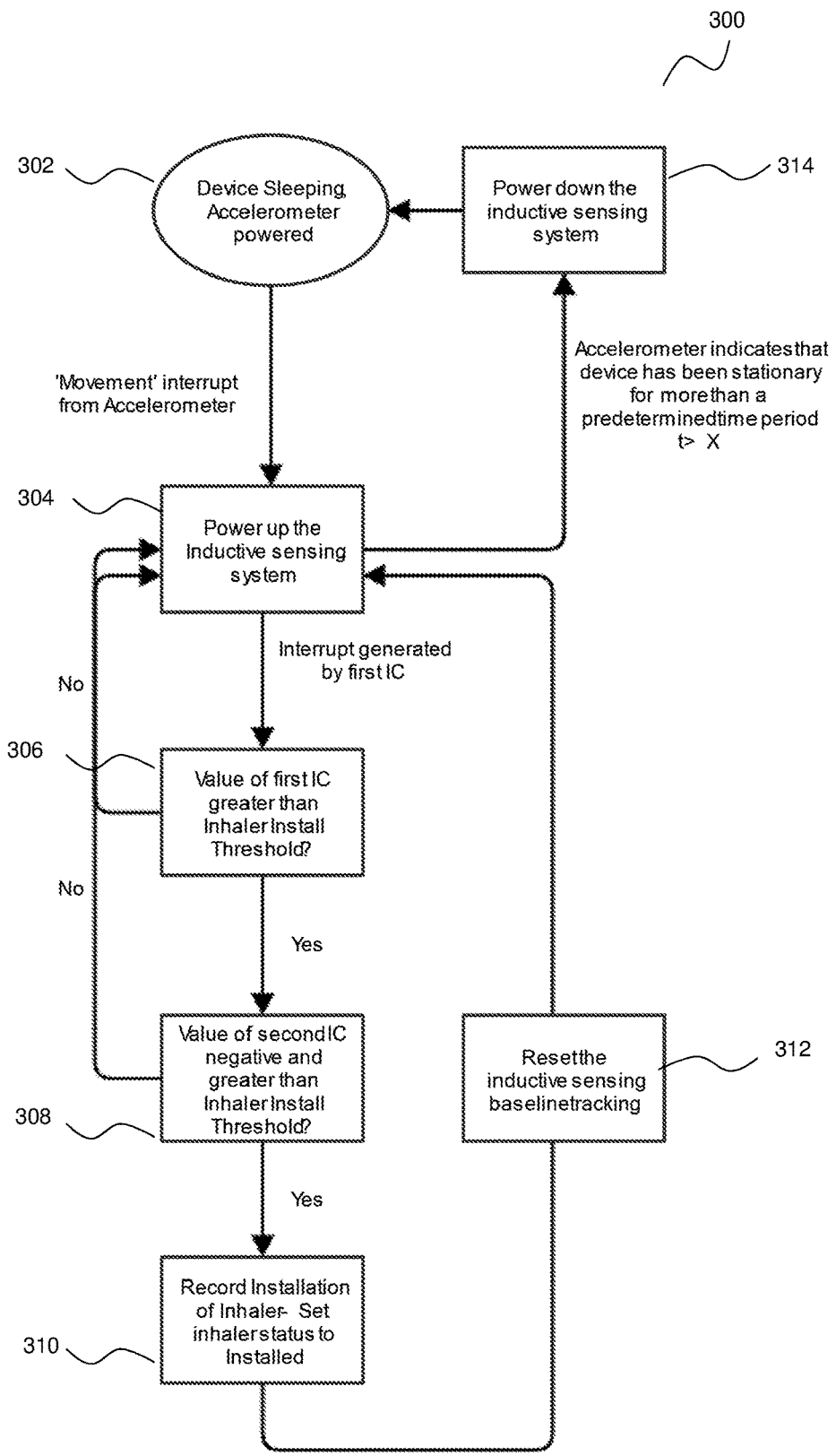
FIG. 13 shows a flowchart of an exemplary process 300 that an inductive coil sensor (ICS) or a processor may use to detect and log installation of an inhaler or medication delivery device into an adherence monitoring device.

FIG. 13 illustrates an exemplary process 300 that the ICS may use to detect installation of the inhaler or medication delivery device (MDD) from the adherence monitoring device. In a first step 302 the ECM may be configured to detect movement of the adherence monitoring device, for example an accelerometer may detect movement of the adherence monitoring device. Upon positive detection of movement of the device, the inductive coil sensor (ICS) system may be activated or provided with power in step 304. If, at step 306, the ICS receives an output from a first coil which is greater than the inhaler install threshold (or MDD install threshold) and at step 308 the output of a second coil is negative and greater in magnitude than the inhaler install threshold (or MDD install threshold), then the ICS or the ECM records installation of the inhaler or the MDD at step 310. Once the inhaler status is set to 'installed', the ICS resets the inductive sensing baseline tracking in step 312 and reverts to ICS powered up status 304. If the output from the first coil in step 306 is below the inhaler install threshold or if the output value of the second IC is not negative and greater in magnitude than the inhaler install threshold, the ICS returns to the activated state 304. The ICS is powered down in step 314, following a signal from the accelerometer indicative of the adherence monitor device being stationary for more than a predetermined t>X.

Figure 14:
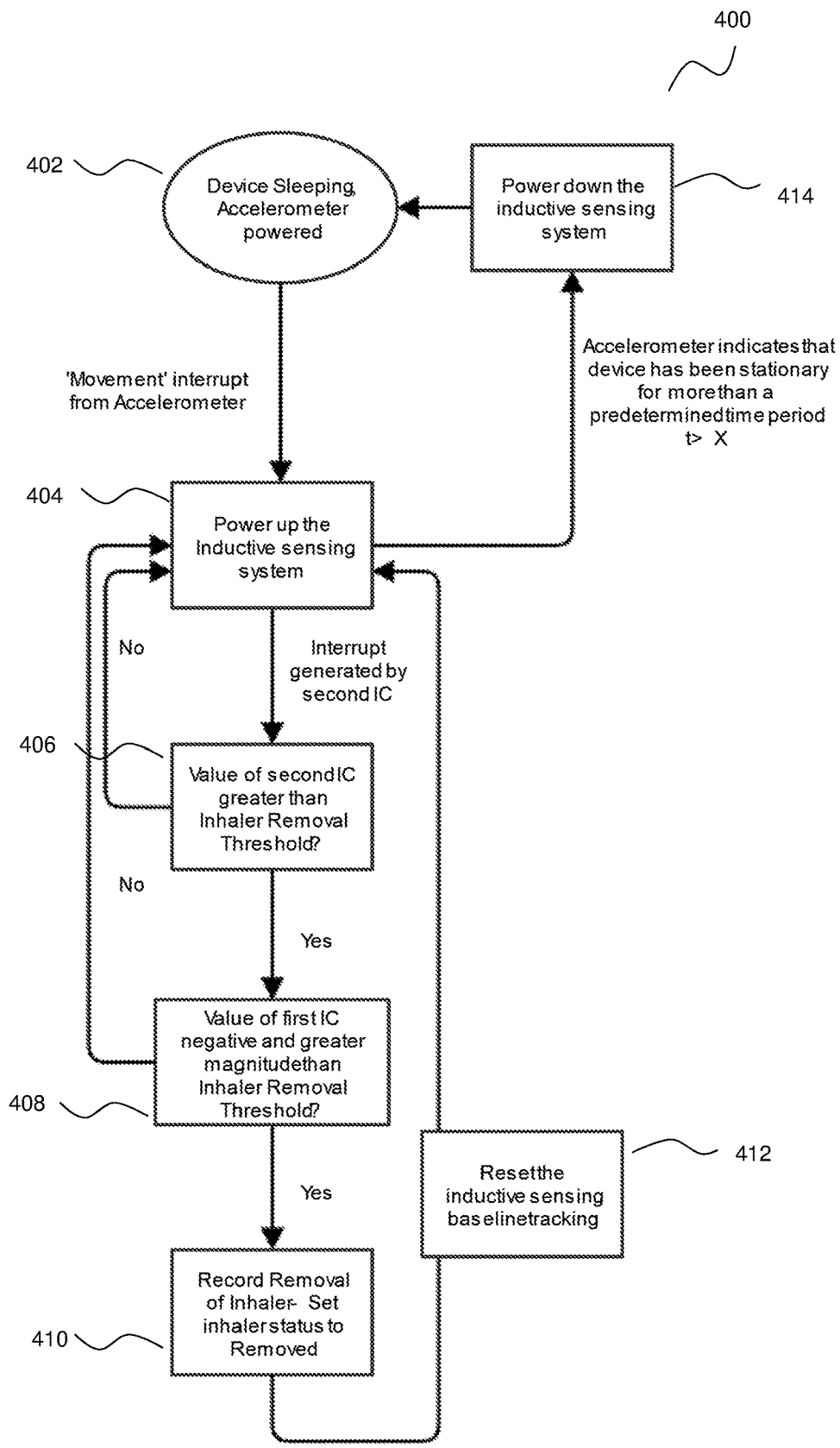
FIG. 14 shows a flowchart of an exemplary process 400 that an ICS or a processor may use to detect and log removal of an inhaler or a medication delivery device from an adherence monitoring device of the present invention.

FIG. 14 illustrates an exemplary process 400 that the ICS may use to detect the removal of the inhaler or MDD form the adherence monitoring device. In a first step 402 the ECM may be configured to detect movement of the adherence monitoring device, for example an accelerometer may detect movement of the adherence monitoring device. Upon positive detection of movement of the device, the inductive coil sensor (ICS) system may be activated or provided with power in step 404. If, at step 406, the ICS receives an output from a second coil which is greater than the inhaler removal threshold (or MDD removal threshold) and at step 408 the output of a first coil is negative and greater in magnitude than the inhaler removal threshold or (MDD removal threshold), then the ICS or the ECM records removal of the inhaler (or MDD) from the device at step 410. Once the inhaler status is set to 'removed', the ICS resets the inductive sensing baseline tracking in step 412 and reverts to ICS powered up status 404. If the output from the second coil in step 406 is below the inhaler removal threshold or if the output value of the first IC is not negative and greater in magnitude than the inhaler removal threshold, the ICS returns to the activated state 404. The ICS is powered down in step 414, following a signal from the accelerometer indicative of the adherence monitor device being stationary for more than a predetermined t>X.

In some embodiments the detection of installation or removal of the inhaler or medication delivery device to or from the adherence monitoring device may use a different sensing system, such a mechanical switch, optical sensors or other such know sensing systems. In such arrangements the ICS system may be used for detection of medication usage events. Consequently, the ICS system may be activated, provided power, after successful detection of the installation of the inhaler or medication delivery device to the adherence monitoring device and/or the ICS system may be deactivated after removal of the inhaler or medication delivery device from the adherence monitoring device is detected. This may reduce the power usage by the adherence monitoring device.

Figure 15:
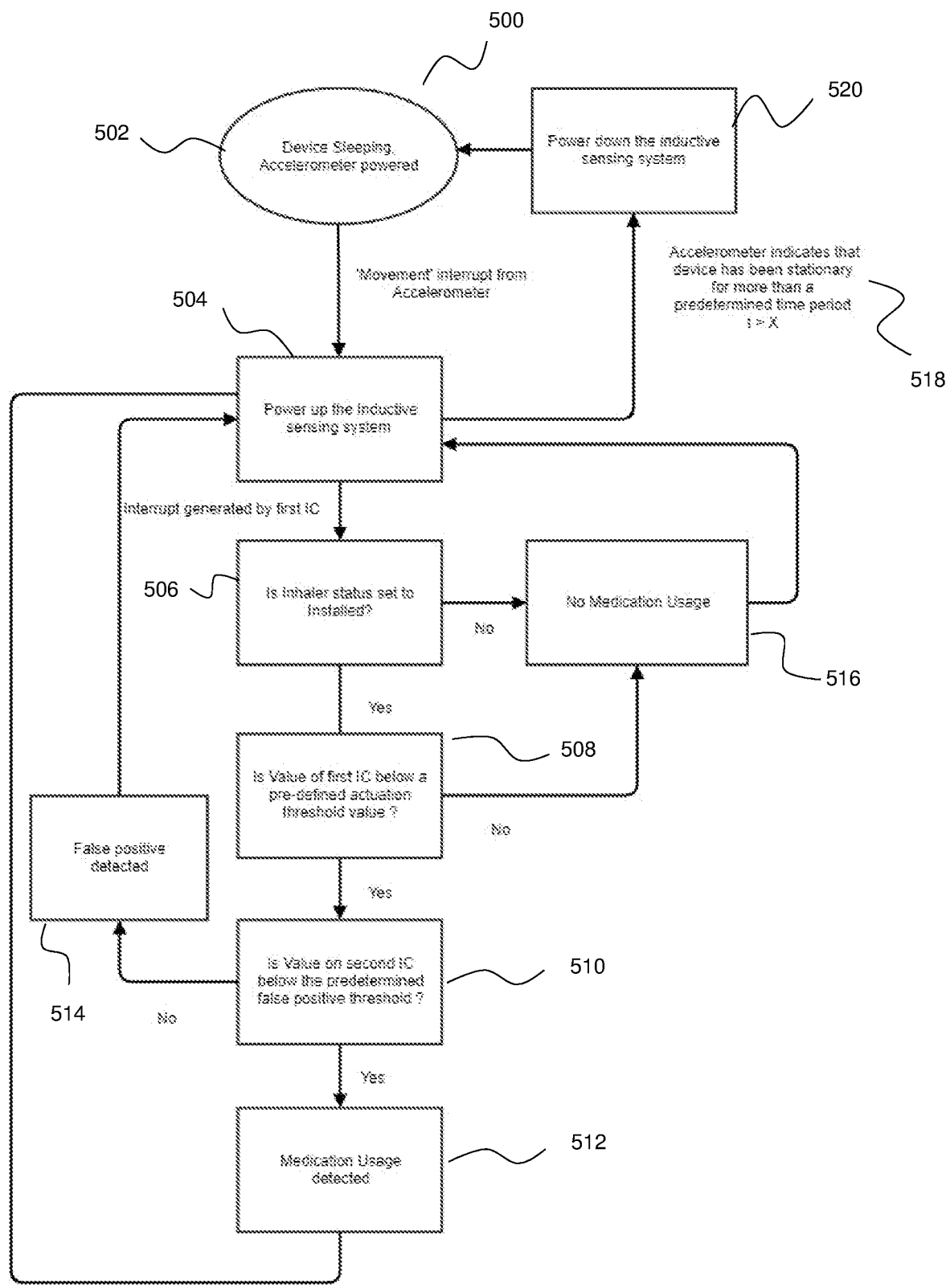
FIG. 15 shows a flowchart of an exemplary process 500 that an ICS or a processor may use to detect and log a medication usage event.

FIG. 15 illustrates an exemplary process 500 that the ICS may use to detect medication usage event. In a first step 502 the ECM may be configured to detect movement of the adherence monitoring device, for example an accelerometer may detect movement of the adherence monitoring device. Upon positive detection of movement of the device, the inductive coil sensor (ICS) system may be activated or provided with power in step 504. Once an interrupt from a first coil is generated, the ICS checks for inhaler or MDD installed status at step 506. If no MDD "installed" status is detected, the ECM does not record medication usage. If the MDD remains stationary for longer than the predetermined period t>X (518), the ICS is powered down in step 520. If the MDD installed status is established in step 506 and the output value from a first coil is below the pre-defined medication actuation threshold value at step 508, the ICS tests for output from a second coil in step 510. If the output value from the second coil is below the predetermined false positive threshold, the ICS or ECM logs the medication actuation or medication usage event at step 512. If the output of the second coil is at or above the predetermined false positive, false positive is detected and logged at step 514.

Figure 16:
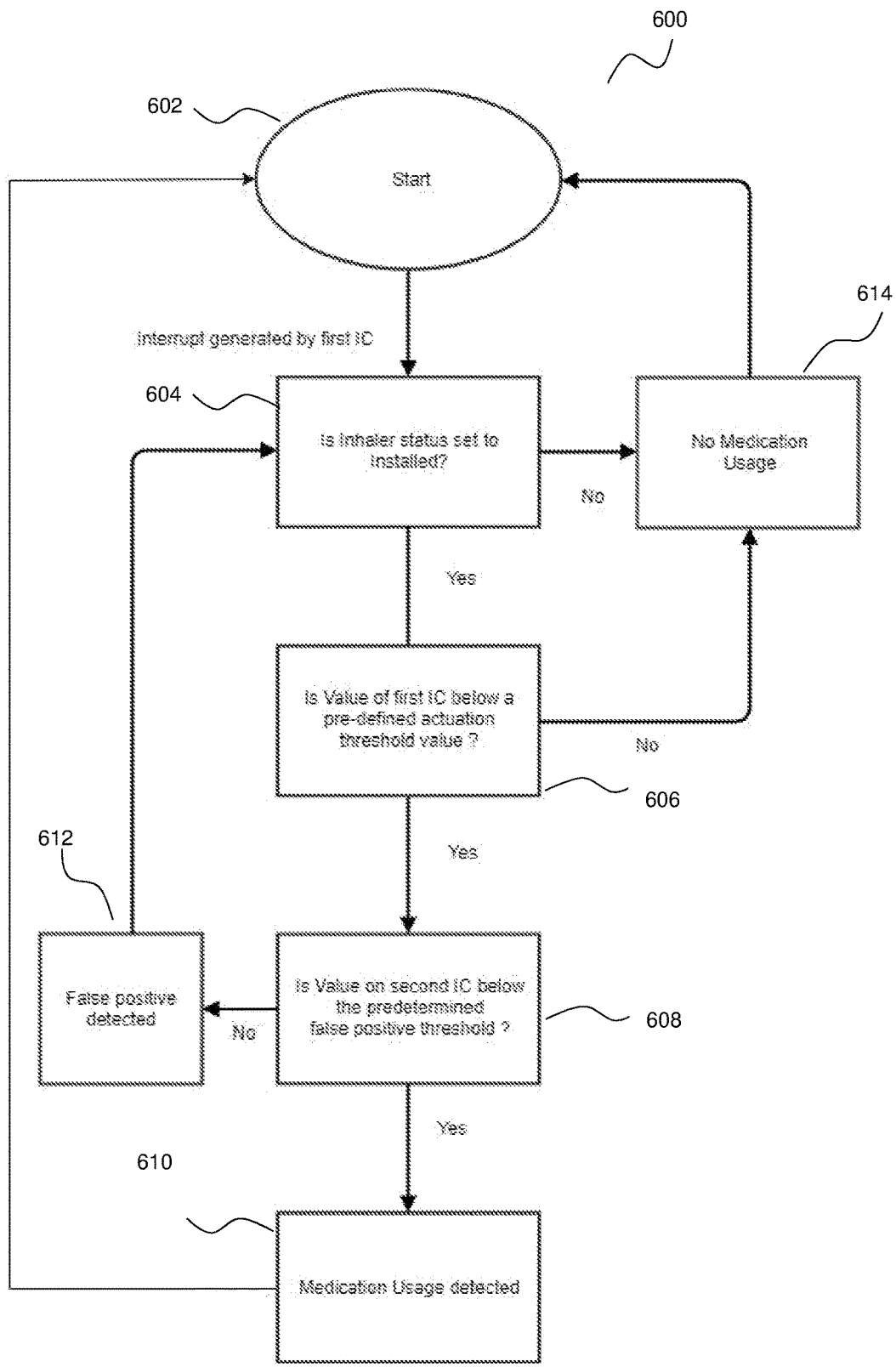
FIG. 16 shows a flowchart of another exemplary process 600 that an ICS or a processor may use to detect and log a medication usage event.

FIG. 16 illustrates another exemplary process 600 that the ICS may use to log and detect medication usage event or a non-medication usage event (false positive). In a first step 602 the ICS is activated through an earlier process. When the interrupt is generated by the first inductive coil, the ICS checks for inhaler or MDD installed status at step 604. If no MDD "installed" status is detected, the ECM does not record medication usage. If the MDD installed status is established in step 604 and the output value from a first coil is below the pre-defined medication actuation threshold value at step 606, the ICS tests for output from a second coil in step 608. If the output value from the second coil is below the predetermined false positive threshold, the ICS or ECM logs the medication actuation or medication usage event at step 610. If the output of the second coil is at or above the predetermined false positive, false positive is detected and logged at step 612.

Figure 17:
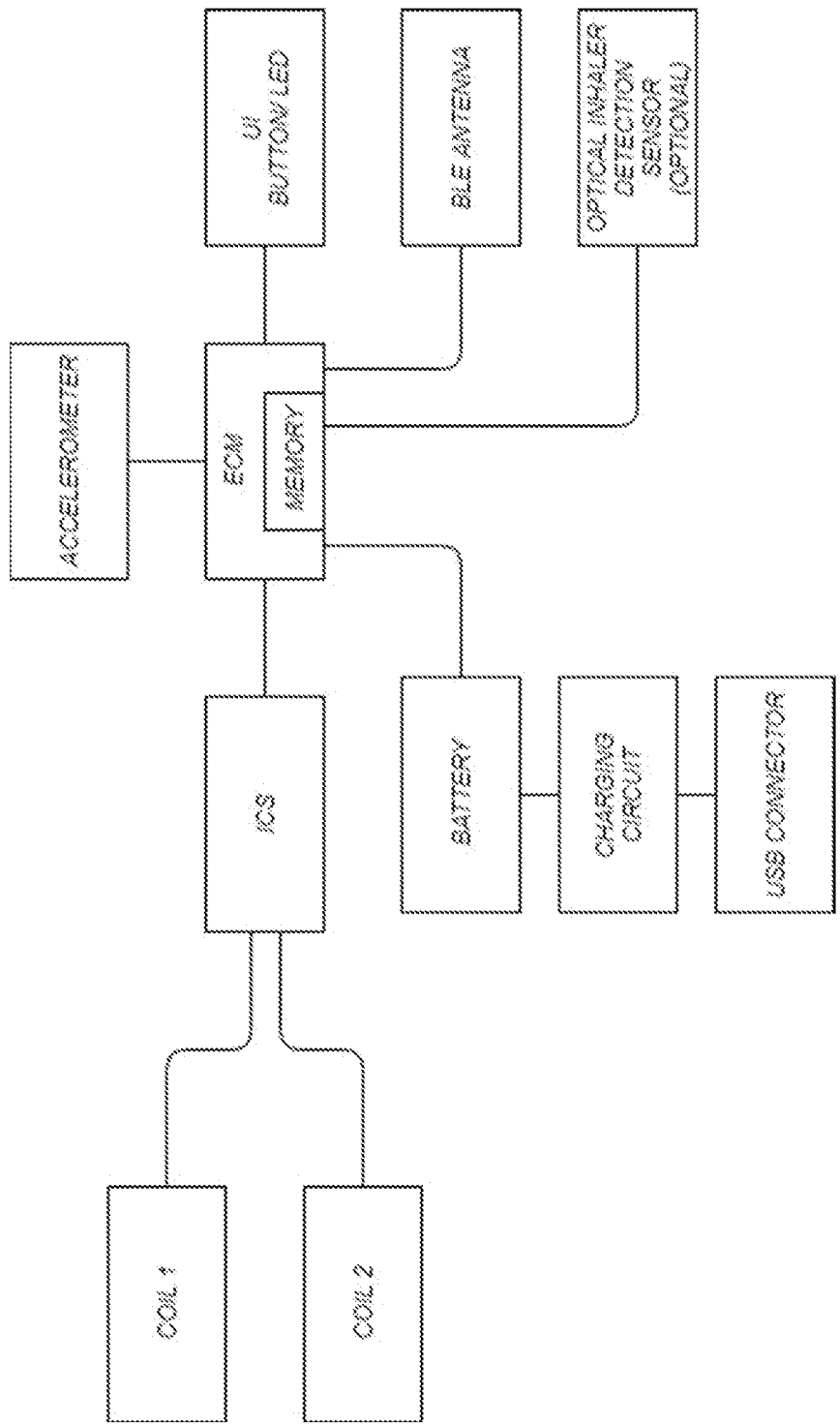
FIG. 17 shows an exemplary circuit layout of an adherence monitoring device of a further embodiment.

Referring to FIG. 17, an example of a circuit layout used in the adherence monitoring device of a further embodiment. Those skilled in the art will appreciate that some or all of the circuit blocks in the exemplary circuit can be present in the integrated circuit in any embodiment of the present invention. Additional circuit blocks can also be included in certain embodiments.

The exemplary circuit includes a first and a second inductive coil configured to exhibit response to an inductive change and to provide change signals in response to the inductive change; an inductive coil sensor (ICS) or inductive controller, for receiving and transmitting the signals from the coils; an accelerometer configured to provide signals to the processor in response to the movement of the adherence monitoring device; a processor (EMC) configured to: receive ICS sensor data, to compare at least one characteristic of the signals from the first coil and the second coil to detect the occurrence of a medication usage event or a false triggering event and to receive output from other sensors: e.g., accelerometer. The exemplary circuit also includes a BLE antenna for wireless transmission of the adherence data gathered to smartphone, tablet or personal computer for further storage of the adherence data on a website database or cloud computing network. The exemplary circuit further includes: a power supply system including a battery and, optionally, a charging circuit and a USB connector (for rechargeable adherence monitoring devices) a memory for storing and reading the processor data. The exemplary circuit also includes a user interface for enabling the user to access data recorded or received by the adherence monitoring device and also change the settings of the adherence monitoring device (for example, date/time, visual/audio alert settings). Some embodiments of the adherence monitoring device circuit layout can also include other sensors, for example, an optical inhaler detection sensor.

FIG. 18A-F are plots showing measured coil inductance of a first and a second inductive coil in response to various inductive change events in an embodiment where the invention is arranged to operate with a pMDI. Plots of normalised inductance against time are shown.

FIG. 18A is a plot showing comparison of magnitude of the signal output of the first (Coil 1) and the second (Coil 2) inductive coils in response to a delivery based inductive change caused by the depression of the pMDI canister during the normal actuation of the pMDI inhaler (as illustrated in FIGS. 3 and 4). During the depression of the canister, the electrically conductive material of the medicament canister changes proximity relative to the first coil. The second inductive coil is coupled to the housing of the adherence monitoring device at a position where the effect of the delivery based inductive change is reduced. The attenuated characteristic of the Coil 2 signal is the strength or magnitude of the signal relative to the signal from Coil 1.

FIG. 18B illustrates the function of time and magnitude of the signal output of the first (Coil 1) and the second (Coil 2) inductive coils in response to an inductive change caused by a slow depression of the pMDI canister. As in FIG. 18A, the magnitude characteristic of the signal output of coil 2 is attenuated relative to the magnitude of the signal output of coil 1, and the processor of the present invention is configured to identify the medication dose delivery event.

FIGS. 18C and 18D further illustrate how the inductive coil 1 and coil 2 respond to a false triggering event. The plots show the respective signal magnitude and duration in response to an inductive change caused by: the detection of external metal interference (FIG. 18C) and deflection of the housing (i.e., user squeezing flexible walls of the adherence monitoring device, FIG. 18D). In the instance of the external metal interference the duration and magnitude of the signal from both coils is substantially the same. Where the inductive change is caused by the deflection of the housing, the magnitude of the signal output of coil 2 is greater than the magnitude of the signal output of coil 1.

Figures 18E, 18F:
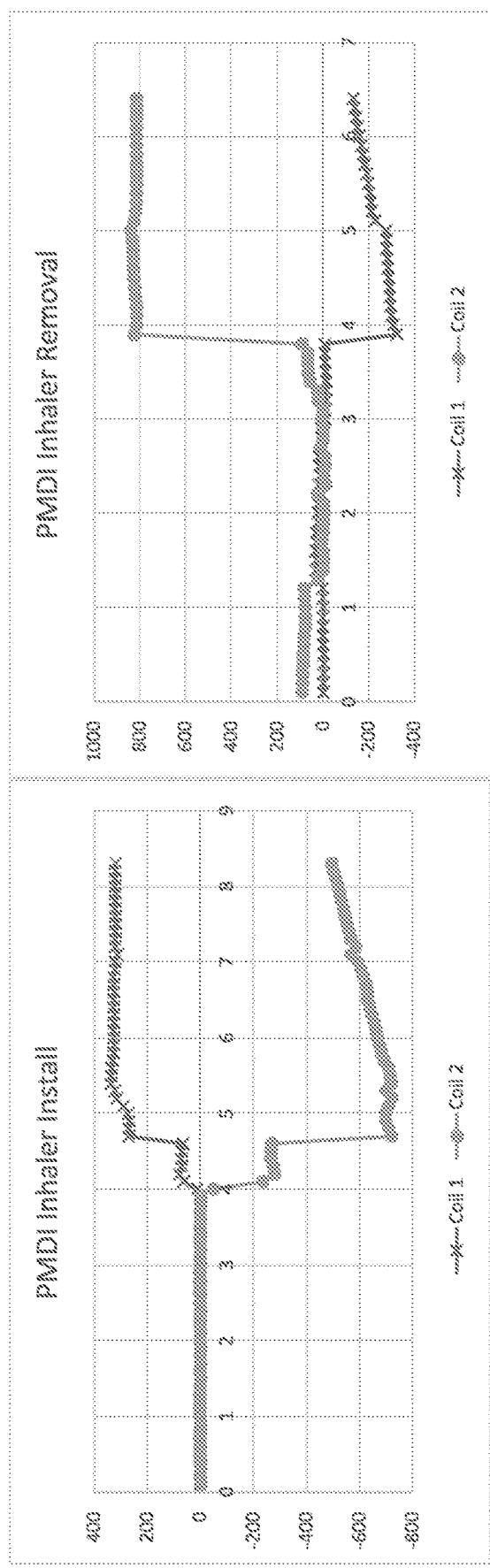

FIGS. 18E and 18F illustrate how the inductive coil 1 and coil 2 respond to a medication usage events that are not delivery based: pMDI installation into (FIG. 18E) and pMDI removal from (FIG. 18F) a releasably attachable embodiment of the adherence monitoring device of the present invention. The duration of the signal, the greater signal magnitude of signal provided by the second coil and the polarity of the signals are characteristic of the inhaler installation and removal.

FIGS. 19A-D are digital representation of inductance against time plots showing change signals provided by a first (Coil 1) and a second (Coil 2) inductive coil in response to an inductive change event in the context of a Respimat® inhaler.

FIGS. 19A and 19B are plots of signal output from coil 1 and coil 2 during the installation and removal of a Respimat® inhaler into and from a releasably attachable embodiment of the adherence monitoring device of the present invention, illustrated in FIGS. 9B-9D. The greater signal magnitude of the signal provided by the second coil relative to the change signal from the first coil and the polarity of the signals are characteristics of the inhaler installation and removal.

Once the inhaler is installed into the adherence monitoring device of the invention, the inductive coils coupled to the housing can detect medication usage events in relation to the inhaler.

FIG. 19C is a plot showing comparison of the magnitude of the voltage signal output of the first (Coil 1) and the second (Coil 2) inductive coils in response to a delivery based inductive change caused by a change of the proximity of the folded spring contained within in the base of the inhaler (as shown by arrow 20 in prior art FIGS. 8A and 8B) relative to the first inductive coil, when the medication container (as shown by arrow 21 in prior art FIGS. 8A and 8B) is loaded for dosing and presses the folded spring and the piercing element towards the first inductive coil.

FIG. 19D is a plot showing a comparison of the magnitude of the signal output of the first (Coil 1) and the second (Coil 2) inductive coils in response to a delivery based inductive change caused by a change of the proximity of the folded spring contained within in the base of the inhaler relative to the first inductive coil during an atomisation process when the dose is triggered. The attenuated characteristic of the Coil 2 signal is the strength or magnitude of the signal relative to signal from Coil 1 and the dose delivery is logged by the processor.

FIGS. 20A-B are normalised digital inductance values against time plots showing change signals provided by a first and a second inductive coil in response to an inductive change event in the context of a Diskus® inhaler. FIG. 20A is a plot showing a comparison of the signal output of a first inductive coil (Coil 1) and a second inductive coil (Coli 2) to the inductive change caused by the opening of the mouthpiece cover (indicated by arrow 34 in prior art FIGS. 5A-5B). FIG. 20B shows the response to the inductive change caused by the closing of said mouthpiece cover. To distinguish between the opening and closing of the mouthpiece cover, the processor is configured to compare the time order of the peaks in the signal amplitude of the change signals received from the first and the second inductive coil. In this instance the characteristic of the change signals being compared by the processor is the time at which the signal peak is reached. The medicament delivery event (opening of the mouthpiece cover) occurs when the second change signal form the second coil occurs later than the first change signal from the first inductive coil.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

In the preceding description and the following claims the word "comprise" or equivalent variations thereof is used in an inclusive sense to specify the presence of the stated feature or features. This term does not preclude the presence or addition of further features in various embodiments.

It is to be understood that the present invention is not limited to the embodiments described herein and further and additional embodiments within the spirit and scope of the invention will be apparent to the skilled reader from the examples illustrated with reference to the drawings. In particular, the invention may reside in any combination of features described herein, or may reside in alternative embodiments or combinations of these features with known equivalents to given features. Modifications and variations of the example embodiments of the invention discussed above will be apparent to those skilled in the art and may be made without departure of the scope of the invention as defined in the appended claims.

While the embodiments described above are currently preferred, it will be appreciated that a wide range of other variations might also be made within the general spirit and scope of the invention.

All patent and other references noted in the specification, including websites, are hereby incorporated by reference.

What we claimed is:

1. An adherence monitoring device for a medication delivery device, the adherence monitoring device comprising:
   a housing;
   at least one inductive coil sensor which includes at least one inductive controller, at least two inductive coils including a first inductive coil coupled to the housing and a second inductive coil coupled to the housing,
   the first inductive coil configured to exhibit a response to an inductive change and provide a first change signal in response to the inductive change, and
   the second inductive coil configured to exhibit a response to the inductive change and provide a second change signal in response to the inductive change; and
   a processor configured to receive sensor data from the inductive controller representative of the first change signal and the second change signal respectively provided by the first inductive coil and second inductive coil, and to compare at least one characteristic of the first change signal to at least one characteristic of the second change signal,
   the comparison being performed to detect the occurrence of a medication usage event or a false triggering event.

2. The adherence monitoring device according to claim 1, wherein the change signal of the first inductive coil and the change signal of the second inductive coil are compared to determine an identity of a type of medication usage event that has occurred.

3. The adherence monitoring device according to claim 1, wherein the medication usage event includes at least one of attachment or removal of a medication delivery device to or from the adherence monitoring device and insertion or removal of a medication container or a medication delivery event.

4. The adherence monitoring device according to claim 1, wherein false triggering events include detection of external metal interference, external electromagnetic field interference or deflection of the housing.

5. The adherence monitoring device according to claim 1, wherein the first inductive coil and second inductive coil are positioned at different locations of the housing.

6. The adherence monitoring device according to claim 1, the medication usage event including a medication delivery event; and
   wherein the inductive change is a delivery based inductive change caused by a change in proximity of an electrically conductive material of the medication delivery device during the medication delivery event relative to the first inductive coil, and the processor is configured to determine the occurrence of the medication delivery event when the at least one characteristic of the second change signal is an attenuated characteristic compared to the at least one characteristic of the first change signal.

7. The adherence monitoring device according to claim 6, wherein the medication delivery event includes at least one of opening or closing of a mouthpiece cap, medication delivery device priming, and medication release or medication delivery.

8. The adherence monitoring device according to claim 6, wherein a position at which the second inductive coil is coupled to the housing results in the second inductive coil exhibiting the attenuated characteristic in response to the delivery based inductive change.

9. The adherence monitoring device according to claim 1, wherein at least one inductive coil is a flat coil.

10. The adherence monitoring device according to claim 1, wherein at least one inductive coil is formed on a substrate, the substrate being included within or upon the housing.

11. The adherence monitoring device according to claim 10, wherein the substrate is a flexible substrate.

12. The adherence monitoring device according to claim 10, wherein the substrate is a printed circuit board or PCB.

13. The adherence monitoring device according to claim 10, wherein the at least one inductive controller is formed on or within the substrate.

14. The adherence monitoring device according to claim 1, wherein the at least one inductive controller is configured to receive the first change signal from the first inductive coil and the second change signal from the second inductive coil and convert the first and second change signals into digital sensor data.

15. The adherence monitoring device according to claim 1, wherein the housing is removably attached to the medication delivery device.

16. The adherence monitoring device according to claim 1, wherein the housing is integrated with at least a portion of the medication delivery device.

17. A method of recording the occurrence of a medication usage event of a medication delivery device using an adherence monitoring device, the method comprising:
   receiving a first change signal from a first inductive coil
   receiving a second change signal from a second inductive coil
   identifying at least one characteristic of the first change signal sourced from the first inductive coil of the adherence monitoring device in response to an instance of an inductive change and identifying at least one characteristic of the second change signal sourced from the second inductive coil of the adherence monitoring device in response to the same instance of inductive change;
   comparing the at least one characteristic of the first and second change signals to determine the occurrence and identity of a medication usage event or detect the occurrence of a false triggering event; and
   recording the occurrence of the identified medication usage event when no false triggering event is determined to have occurred.

18. A method of recording occurrence of a medication delivery event of a medication delivery device using an adherence monitoring device, the method comprising:
   receiving a first change signal from a first inductive coil
   receiving a second change signal from a second inductive coil
   identifying at least one characteristic of the first change signal sourced from the first inductive coi of the adherence monitoring device in response to an instance of inductive change and identifying at least one characteristic of the second change signal sourced from the second inductive coil of the adherence monitoring device in response to the same instance of inductive change;

comparing the at least one characteristic of the first and second change signals to determine if the at least one characteristic of the second change signal is an attenuated characteristic; and recording the completion of a medication delivery event if the second change signal exhibits an attenuated characteristic.

19. A non-transitory computer readable storage media storing computer executable instructions configured to implement a method of recording medication usage events by:

identifying at least one characteristic of a first change signal sourced from a first inductive coil of the adherence monitoring device in response to an instance of inductive change and identifying at least one characteristic of a second change signal sourced from a second inductive coil of the adherence monitoring device in response to the same instance of inductive change;

comparing the at least one characteristic of the first and second change signals to determine the occurrence and identity of a medication usage event or detect the occurrence of a false triggering event; and recording the occurrence of the identified medication usage event when no false triggering event is determined to have occurred.

20. A non-transitory computer readable storage media storing computer executable instructions configured to implement a method of recording medication delivery events by:

identifying at least one characteristic of a first change signal sourced from a first inductive coil of the adherence monitoring device in response to an instance of inductive change and identifying at least one characteristic of a second change signal sourced from a second inductive coil of the adherence monitoring device in response to the same instance of inductive change;

comparing the at least one characteristic of the first and second change signals to determine the second inductive coil is an attenuated characteristic; and recording the completion of a medication delivery event if the second change signal exhibits an attenuated characteristic.

* * * * *